(12) United States Patent
Brown et al.

(10) Patent No.: US 9,089,572 B2
(45) Date of Patent: Jul. 28, 2015

(54) INHIBITORS OF P97

(75) Inventors: Steven J. Brown, San Diego, CA (US);
Tsui-Fen Chou, Pasadena, CA (US);
Raymond Deshaies, Claremont, CA (US); Amanda C. Jones, Pasadena, CA (US); Hugh Rosen, La Jolla, CA (US);
Brian M. Stoltz, San Marino, CA (US)

(73) Assignees: California Institute of Technology, Pasadena, CA (US); The Scripps Research Institute, La Jolla, CA (US)

(*) Notice: Subject to any disclaimer, the term of this patent is extended or adjusted under 35 U.S.C. 154(b) by 1402 days.

(21) Appl. No.: 12/321,463

(22) Filed: Jan. 20, 2009

(65) Prior Publication Data

US 2009/0253717 A1      Oct. 8, 2009

Related U.S. Application Data

(60) Provisional application No. 61/011,436, filed on Jan. 17, 2008, provisional application No. 61/134,174, filed on Jul. 7, 2008.

(51) Int. Cl.
*A61K 31/519* (2006.01)
(52) U.S. Cl.
CPC ................................ *A61K 31/519* (2013.01)
(58) Field of Classification Search
None
See application file for complete search history.

(56) References Cited

U.S. PATENT DOCUMENTS

| 5,760,041 A | 6/1998 | Wisner et al. | |
|---|---|---|---|
| 2003/0129186 A1* | 7/2003 | Beliveau et al. | 424/144.1 |
| 2010/0222408 A1* | 9/2010 | Zeitlin et al. | 514/44 A |

OTHER PUBLICATIONS

Vippagunta et al., Advanced Drug Delivery Reviews, 48 (2001), pp. 3-26.*
Blair, Jimmy A., et al; "Structure-guided development of affinity probes for tyrosine kinases using chemical genetics." Nature Chemical Biology, vol. 3 No. 4; Apr. 2007 p. 229-238.
De, Nimai C., et al; "The Rearrangements of 2-Amino-*N*—1*H*-pyrazolo [3,4-*d*] pyrmidin-4-yl-acetamide and 2-Amino-*N*-4-pyrimidinylacetamide." J.C.S. Perkin I, 1979.
Gamage, Swarna A., et al.; "Phenazine-1-carboxamides: Structure-cytotoxicity relationships for 9-substituents and changes in the H-bonding pattern of the cationic side chain." Bioorganic & Medicinal Chemistry 14 (2006) 1160-1168.
Jellali, M. El Hedi; et al; "Sur L'Acylation Et L'Alkylation De L'Amino-4 Pyrazolo [3,4-d] Pyrimidine" Tetrahedron vol. 31, pp. 587 to 591 (1975).
Mishani, Eyal, et al.; "High_Affinity Epidermal Growth Factor Receptor (EGFR) Irreversible Inhibitors with Diminished Chemical Reactivities as Positron Emission Tomography (PET)-Imaging Agent Candidates of EGRF Overexpressing Tumors." J. Med. Chem. 2005, 48 5337-5348.
Smaill, Jeff B., "Tyrosine Kinase Inhibitors. 15. 4-(Phenylamino) quinazoline and 4-(Phenylamino) pyrido [d]pyrimidine Acrylamides as Irreversible Inhibitors of the ATP Binding Site of the Epidermal Growth Factor Receptor." J. Med. Chem. 1999, 42, 1803-1815.
Annunziata, Christina M. et. al.; "Frequent engagement of the classical and alternative NF-κB pathways by diverse genetic abnormalities in multiple myeloma"; Cancer Cell; Aug. 2007; vol. 12; No. 12; pp. 115-130.
Berge, Stephen M. et al.; "Pharmaceutical Salts"; J. Pharm. Sci.; Jan. 1977; vol. 66; No. 1; pp. 1-19.
Boelens, Jerina et al.; "The Endoplasmic Reticulum: A Target for New Anticancer Drugs"; In Vivo; 2007; vol. 21; pp. 215-226.
Cao, Kan et al.; "The AAA-ATPase Cdc48/p97 Regulates Spindle Disassembly at the End of Mitosis"; Cell; Oct. 31, 2003; vol. 115; pp. 355-367.
Carvalho, Pedro et al.; "Distinct Ubiquitin-Ligase Complexes Define Convergent Pathways for the Degradation of ER Proteins"; Cell; Jul. 28, 2006; vol. 126; pp. 361-373.
Dai, Ren-Ming et al.; "Protein Chemistry and Structure: Involvement of Valosin-containing Protein, an ATPase Co-purified with I κBα and 26 S Proteasome, in Ubiquitin-Proteasome-mediated Degradation of I κBα"; J. Biol. Chem.; 1998; vol. 273; pp. 3562-3573.
Delabarre, Byron et al.; "Complete structure of p97/valosin-containing protein reveals communication between nucleotide domains"; Nat. Struct. Biol.; Oct. 2003; vol. 10; No. 10; pp. 856-863.
Fu, Xinrong et al.; "Cdc48p is required for the cell cycle commitment point at Start via degradation of the G1-CDK inhibitor Far1p"; J. Cell Biol.; Oct. 13, 2003; vol. 163; No. 1; pp. 21-26.
Giaever, Guri et. al.; "Functional profiling of the Saccharomyces cerevisiae genome"; Nature; Jul. 25, 2002; vol. 418; pp. 387-391.
Golbik, Ralph et al.; "The Janus Face of the Archaeal Cdc48/p97 Homologue VAT: Protein Folding versus Unfolding"; Biol. Chem.; vol. 380; Sep. 1999; pp. 1049-1062.
Wuts, Peter G.M. et al.; " Greene's Protective Groups in Organic Synthesis", 4th. Ed.; Wiley & Sons; 2006; 1107pp.
Huyton, Trevor et al.; "The crystal structure of murine p97/VCP at 3.6 Å"; Journal of Structural Biology; 2003; vol. 144; pp. 337-348.
Janiesch, Philipp C. et al.; "The ubiquitin-selective chaperone CDC-48/p97 links myosin assembly to human myopathy"; Nat. Cell Biol.; Apr. 2007; vol. 9; No. 4; pp. 379-390.
Keats, Jonathan J. et. al.; "Promiscuous Mutations Activate the Non-Canonical NF-kB Pathway in Multiple Myeloma"; Cancer Cell; Aug. 2007; vol. 12; No. 2; pp. 131-144.
Lanzetta, Peter A. et al.; "An Improved Assay for Nanomole Amounts of Inorganic Phosphate"; Analytical Biochem.; 1979; vol. 100; pp. 95-97.
Meyer, Hemmo H. et al.; "A complex of mammalian Ufd1 and Npl4 links the AAA-ATPase, p97, to ubiquitin and nuclear transport pathways"; The EMBO Journal; 2000; vol. 19, No. 10; pp. 2181-2192.
Müller, J.M.M. et al.; "Targeted deletion of p97 (VCP/CDC48) in mouse results in early embryonic lethality"; Biochem. & Biophys. Res. Commun.; 2007; vol. 354; pp. 459-465.

(Continued)

*Primary Examiner* — Jeffrey S Lundgren
*Assistant Examiner* — Michael Schmitt
(74) *Attorney, Agent, or Firm* — Christie, Parker & Hale, LLP

(57) ABSTRACT

One aspect of the invention relates to compounds that inhibit the activity of p97, such as by binding covalently to a cysteine residue in the active site. In certain embodiments, the invention relates to the treatment of disease, such as cancer, comprising administering a compound of the invention.

5 Claims, 32 Drawing Sheets

(56) References Cited

OTHER PUBLICATIONS

Rabouille, Catherine et al.; "An NSF-like ATPase, p97, and NSF Mediate Cisternal Regrowth from Mitotic Golgi Fragments"; Cell; Sep. 22, 1995; vol. 82; pp. 905-914.

Richly, Holger et al.; "A Series of Ubiquitin Binding Factors Connects CDC48/p97 to Substrate Multiubiquitylation and Proteasomal Targeting"; Cell; Jan. 14, 2005; vol. 120; pp. 73-84.

Song, Changcheng et al.; "Enzyme Catalysis and Regulation: ATPase Activity of p97-Valosin-containing Protein (VCP): D2 Mediates the Major Enzyme Activity, and D1 Contributes to the Heat-Induced Activity"; J. Biol. Chem.; 2003; vol. 278; pp. 3648-3655.

Wang, Xiaorong et al.; "Mass Spectrometric Characterization of the Affinity-Purified Human 26S Proteasome Complex"; Biochemistry; 2007; vol. 46; pp. 3553-3565.

Wang, Qing et al.; "Hexamerization of p97-VCP is promoted by ATP binding to the D1 domain and required for ATPase and biological activities"; Biochem. & Biophys. Res. Commun.; 2003; vol. 300; pp. 253-260.

Wein L, Conrad C. et al.; "Inclusion body myopathy-associated mutations in p97/VCP impair endoplasmic reticulum-associated degradation"; Hum. Mol. Genet.; 2006; vol. 15; No. 2; pp. 189-199.

Wójcik, Cezary et al.; "RNA interference of valosin-containing protein (VCP/p97) reveals multiple cellular roles linked to ubiquitin/proteasome-dependent proteolysis"; J. Cell Sci.; 2003; vol. 117; pp. 281-292.

Wójcik, Cezary et al.; "Valosin-containing Protein (p9'7) Is a Regulator of Endoplasmic Reticulum Stress and of the Degradation of N-End Rule and Ubiquitin-Fusion Degradation Pathway Substrates in Mammalian Cells"; Mol. Biol. Cell; Nov. 2006; vol. 17; pp. 4606-4618.

Yamamoto, Shinji et al.; "Increased Expression of Valosin-Containing Protein (p97) is Associated With Lymph Node Metastasis and Prognosis of Pancreatic Ductal Adenocarcinoma"; Ann. Surg. Oncol.; 2004; vol. 11; No. 2; pp. 165-172.

Yamamoto, Shinji et al.; "Expression Level of Valosin-Containing Protein (p97) Is Correlated With Progression and Prognosis of Non—Small-Cell Lung Carcinoma"; Ann. Surg. Oncol.; 2004; vol. 11; No. 7; pp. 697-704.

Yamamoto, Shinji et al.; "Increased Expression of Valosin-Containing Protein (p97) Is Correlated With Disease Recurrence in Follicular Thyroid Cancer"; Ann. Surg. Oncol.; 2005; vol. 12; No. 11; pp. 925-934.

Yamamoto, Shinji et al.; " Expression Level of Valosin-Containing Protein (p97) Is Associated with Prognosis of Esophageal Carcinoma"; Clin. Cancer Res.; Aug. 15, 2004; vol. 10; pp. 5558-5565.

Ye, Yihong. et al; "The AAA ATPase Cdc48/p97 and its partners transport proteins from the ER into the cytosol"; Nature; vol. 414; Dec. 6, 2001; pp. 652-656.

Ye, Yihong, et al.; "Function of the p97-Ufd1-Np14 complex in retrotranslocation from the ER to the cytosol: dual recognition of the nonubiquitinated polypeptide segments and polyubiquitin chains"; J. Cell Biol.; vol. 162, No. 1; Jul. 7, 2003; pp. 71-84.

Ye, Yihong, et al.; "A membrane protein complex mediates retrotranslocation from the ER lumen into the cytosol"; Nature; Jun. 24, 2004; vol. 429; pp. 841-847.

* cited by examiner

Amino Acid Sequence Alignment of AAA ATPase in Walker A motif

```
Murine p97 D1    YGPPGTGKTL
Murine P97 D2    YGPPGCGKTL
Yeast Cdc48 D1   YGPPGTGKTL
Yeast Cdc48 D2   YGPPGTGKTL
Hamster NSF D1   YGPPGCGKTL
Hamster NSF D2   EGPPHSGKTA
Human Rpt1       FGPPGTGKTL
Human Rpt2       YGPPGTGKTL
Human Rpt3       YGPPGCGKTM
Human Rpt4       YGPPGTGKTL
Human Rpt5       YGPPGTGKTL
Human Rpt6       YGPPGTGKTL
```

Figure 3

INHIBITORS OF P97

CROSS-REFERENCE TO RELATED APPLICATIONS

This application claims the benefit of U.S. Provisional Application Nos. 61/011,436, filed Jan. 17, 2008, and 61/134,174, filed Jul. 7, 2008. The contents of these applications are incorporated herein by reference in their entirety.

STATEMENT REGARDING FEDERALLY SPONSORED RESEARCH OR DEVELOPMENT

This invention was made with government support under Grant Numbers AI-055509, AI-074564 and MH-074404 awarded by the National Institutes of Health. The government has certain rights in the invention.

BACKGROUND OF THE INVENTION

The AAA (ATPase associated with a variety of activities) ATPase p97 is conserved across all eukaryotes and is essential for life in budding yeast (Giaever, G., et. al. *Nature* (2002) 418, 387-391) and mice (Muller, J. M. et al. *Biochem. Biophys. Res. Commun.* (2007) 354, 459-465). Humans bearing reduction-of-function alleles of p97 are afflicted with a syndrome that includes inclusion body myopathy and frontotemporal lobar degeneration (Weihl, C. et al. *Hum. Mol. Genet.* (2006) 15, 189-199). Loss-of-function studies in model organisms indicate that p97 plays a critical role in a broad array of cellular processes including Golgi membrane reassembly (Rabouille, C. et al. *Cell* (1995) 82, 905-914), membrane transport (Ye, Y. et al *Nature* (2001) 414, 652-656; Ye, Y. et al. *Nature* (2004) 429, 841-847) degradation of misfolded membrane and secretory proteins by the ubiquitin-proteasome system (UPS) (Golbik, R. et al. *Biol. Chem.* (1999) 380, 1049-1062; Richly, H. et al. *Cell* (2005) 120, 73-84), regulation of myofibril assembly (Janiesch, P. C. et al. *Nat. Cell Biol.* (2007) 9, 379-390), and cell division (Cao, K. et al. *Cell* (2003) 115, 355-367). The broad range of cellular functions for this protein are thought to derive from its ability to unfold proteins or disassemble protein complexes. The mechanochemical activity of p97 is linked to substrate proteins by an array of at least 14 UBX domain adapters that bind p97, as well as the non-UBX domain adaptors Ufd1 and Npl4 (Meyer, H. H. et al. *EMBO J.* (2000) 19, 2181-2192).

The sequence of p97 reveals three domains (N-domain, D1 ATPase domain, and D2 ATPase domain) joined by linker regions. X-ray crystallography of p97 revealed that it forms a homohexamer of 97 kilodalton subunits that assemble to form two stacked rings. The two rings are formed by the ATPase domains (Huyton, T. et al. *Jan.* 16, 2009. *Struct. Biol.* (2003) 144, 337-348; DeLaBarre, B. et al. *Nat. Struct. Biol.* (2003) 10, 856-863). The 'top' ring is formed by a hexamer of the D1 domains, whereas the 'bottom' ring is formed by a hexamer of the D2 domains. The N-domain extends outward from the D1 domain ring. Although it is clear that the D2 domain hydrolyzes ATP in vitro, the level of D1-specific ATPase activity reported by different investigators varies. Nevertheless, genetic studies in yeast suggest that ATP hydrolysis by both the D1 and D2 domains is essential for the function of p97 (Song, C. et al. *J. Biol. Chem.* (2003) 278, 3648-3655; Ye, Y. et al. *J. Cell Biol.* (2004) 162, 71-84). Binding of ATP to the D1 domain is also required for assembly of p97 (Wang, Q. et al. *Biochem. Biophys. Res. Commun.* (2003) 300, 253-260). Although ATP hydrolysis by the D2 domain is not required for assembly of p97 hexamer, it is thought that ATP hydrolysis by the D2 domain is an obligate step in the catalytic cycle of p97, and contributes to structural transformations in bound substrates, resulting in their unfolding or dissociation from bound partners.

A prominent cellular function for p97 that has received considerable scrutiny is its role in the turnover of misfolded secretory proteins via the UPS. In this process, which is known as ERAD (for endoplasmic reticulum-associated degradation), proteins that fail to fold within the ER are retrotranslocated in a p97-dependent manner into the cytoplasm where they are degraded by the UPS (Ye, Y. et al. *Nature* (2004) 429, 841-847). In this process, p97 is thought to mediate extraction of substrates from the ER membrane. p97 is also required for the turnover of cytosolic substrates of the UPS (Janiesch, P. C. et al. *Nat. Cell Biol.* (2007) 9, 379-390; Cao, K. et al. *Cell* (2003) 115, 355-367; Fu, X. et al. *J. Cell Biol.* (2003) 163, 21-26), although its role in turnover of cytosolic proteins is less understood.

p97 represents a suitable target for for cancer therapeutics. p97 is essential, and so drugs that inhibit it should be antiproliferative. Also, p97 is known to be overproduced in multiple cancers (Yamamoto, S. et al. *Ann. Surg. Oncol.* (2005) 12, 925-934; Yamamoto, S. et al. *Clin. Cancer Res.* (2004) 10, 5558-5565; Yamamoto, S. et al. *Ann. Surg. Oncol.* (2004) 11, 697-704; Yamamoto, S. et al. *Ann. Surg. Oncol.* (2004) 11, 165-172) suggesting that its activity may be rate-limiting for the development of at least some cancers. p97 is known to be essential for ERAD (Carvalho, P. et al. *Cell* (2006) 126, 361-373), and recent studies suggest that cancer cells may be particularly dependent upon ERAD (Boelens, J. et al. *In Vivo* (2007) 21, 215-226). Furthermore, p97 has been linked to the turnover of IkB and consequent activation of NF-kB (Dai, R. M. et al. *J. Biol. Chem.* (1998) 273, 3562-3573). NF-kB activity is important for the survival of some tumor cells, particularly in multiple myeloma (Keats, J. J. et. al. *Cancer Cell* (2007) 12, 131-144; Annunziata, C. M. et. al. *Cancer Cell* (2007) 12, 115-130). It has been suggested that bortezomib is active in multiple myeloma due to its ability to block turnover of proteins via the ERAD pathway and its ability to block turnover of IkB, thereby squelching the activity of NF-kB. Given that p97 is implicated in both ERAD and IkB turnover but otherwise has a more restricted role in the UPS compared to the proteasome itself, drugs that target p97 may retain much of the efficacy of bortezomib but with less toxicity.

Thus there exists a need in the art for compounds for and methods of inhibiting the activity of p97.

SUMMARY OF THE INVENTION

One aspect of the invention relates to compounds that inhibit p97. In certain embodiments, the compounds inhibit the ATPase activity of P97. In certain embodiments, the invention relates to the treatment of a disease (e.g., cancer), comprising administering a compound of the invention.

One aspect of the invention relates to compounds having a structure of Formula I or a pharmaceutically acceptable salt thereof, $$\text{Ar-E} \qquad (I)$$

wherein

Ar is selected from substituted or unsubstituted aryl and heteroaryl, optionally a polycyclic aryl or heteroaryl moiety, e.g., naphthalene, anthracene, phenanthrene, quinoline, indole, etc.; and E is an electrophilic group, such as a group capable of interacting with and forming a covalent bond or complex with a nucleophile,
or a pharmaceutically acceptable salt or prodrug thereof.

In certain embodiments, E is selected from

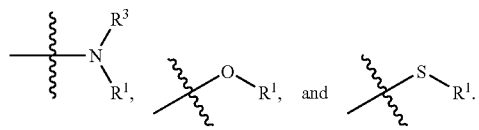

In other embodiments, E is an alkene activated to nucleophilic attack, such as a nitroalkenyl (e.g.,

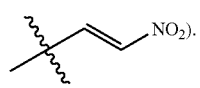

In certain embodiments, $R^1$ and $R^4$, together with the atoms to which they are attached, form one or more rings.

In certain embodiments, $R^1$ is selected from hydrogen, haloalkyl (e.g., chloroalkyl, bromoalkyl, iodoalkyl, e.g.,

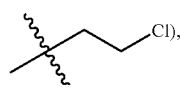

aziridine (e.g.,

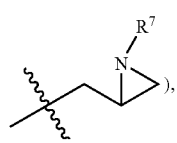

epoxide (e.g.,

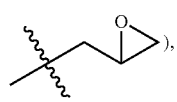 [SMILES: *CC1CO1]

vinyl sulfone (e.g.,

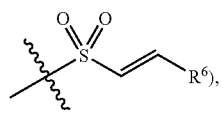

acrylyl (e.g.,

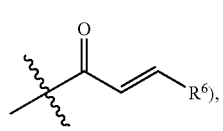

alkenyl (e.g.,

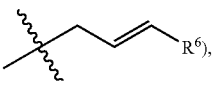

substituted acetyl (e.g.,

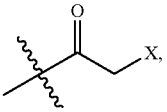

wherein X is a leaving group, e.g., F, Cl, Br, I, —OS(O$_2$)R$^2$, or —OS(O)R$^2$), cyanoalkyl (e.g.,

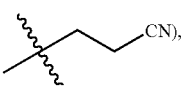

acyl (e.g.,

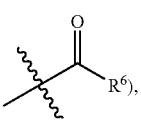

sulfonyl carbonyl (e.g.,

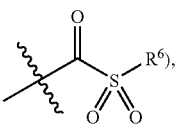

and sulfinyl carbonyl (e.g.,

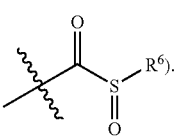

In certain embodiments, $R^1$ has an atom susceptible to nucleophilic attack, e.g., capable of forming a covalent bond with a nucleophile. This atom is preferably within 2-6 atoms of Ar, e.g., within 2-4 atoms, most preferably 3 atoms of Ar.

In certain such embodiments, $R^1$ is selected from haloalkyl (e.g., chloroalkyl, bromoalkyl, iodoalkyl, e.g.,

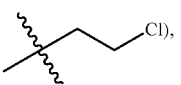

aziridine (e.g.,

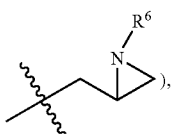), epoxide (e.g.,

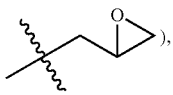), vinyl sulfonyl (e.g.,

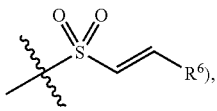), acrylyl (e.g.,

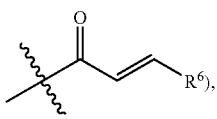), substituted acetyl (e.g.,

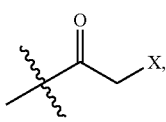, wherein X is selected from F, Cl, Br, I, —OS(O$_2$)R$^2$, and —OS(O)R$^2$).

In certain embodiments, R$^6$ is selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In certain embodiments, R$^6$ is selected from H and substituted or unsubstituted alkyl, heteroalkyl, aralkyl, cycloalkyl, heterocyclyl, aryl, heteroaryl, heteroaralkyl, cycloalkylalkyl, heterocyclylalkyl, or halogen.

In certain embodiments as discussed above, R$^6$ may be substituted by one or more substituents selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, R$^6$ and R$^4$, together with the atoms to which they are attached, form one or more rings.

In certain embodiments, R$^7$ is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido.

In certain embodiments as discussed above, R$^7$ may be substituted by one or more substituents selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, R$^7$ and R$^4$, together with the atoms to which they are attached, form one or more rings.

In certain embodiments, R$^1$ is acrylyl (e.g.,

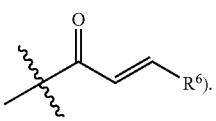).

In certain such embodiments, R$^1$ is H.

In certain embodiments, R$^1$ is substituted acetyl (e.g.,

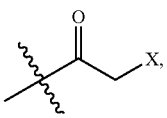, wherein X is selected from Cl, Br, I, —OS(O$_2$)R$^2$, —OS(O)R$^2$). In certain such embodiments, X is Cl.

In certain embodiments, R$^3$ is selected from any of the groups described above for R$^1$, while in other embodiments R$^3$ can be H or substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido.

In certain embodiments, R$^3$ may be substituted by one or more substituents selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $R^3$ and $R^4$, together with the atoms to which they are attached, form one or more rings.

In certain embodiments, $R^3$ is H.

In certain embodiments, $R^3$ is acrylyl (e.g.,

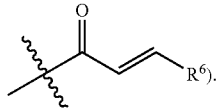

).

In certain such embodiments, $R^6$ is H.

In certain embodiments, Ar is selected from

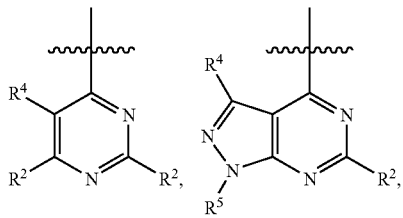

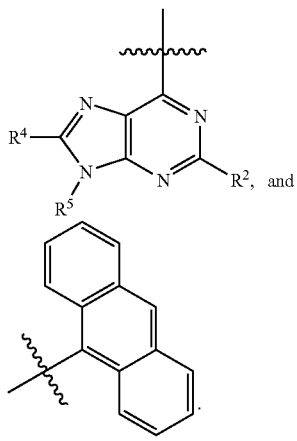

In certain embodiments, independently for each occurrence, $R^2$ is selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In certain embodiments, independently for each occurrence, $R^2$ is selected from H and substituted or unsubstituted alkyl, heteroalkyl, aralkyl, cycloalkyl, heterocyclyl, aryl, heteroaryl, heteroaralkyl, cycloalkylalkyl, heterocyclylalkyl, or halogen.

In certain embodiments as discussed above, $R^2$ may be substituted by one or more substituents selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $R^2$ is H.

In certain embodiments, $R^4$ is selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In certain embodiments, $R^4$ is selected from H and substituted or unsubstituted alkyl, heteroalkyl, aralkyl, cycloalkyl, heterocyclyl, aryl, heteroaryl, heteroaralkyl, cycloalkylalkyl, heterocyclylalkyl, halogen.

In certain embodiments, $R^4$ is aryl (e.g., phenyl or naphthyl (such as beta-naphthyl)).

In certain embodiments as discussed above, $R^4$ may be substituted by one or more substituents selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $R^4$ and $R^1$, together with the atoms to which they are attached, form one or more rings.

In certain embodiments, $R^4$ and $R^3$, together with the atoms to which they are attached, form one or more rings.

In certain embodiments, $R^4$ and $R^6$, together with the atoms to which they are attached, form one or more rings.

In certain embodiments, $R^4$ and $R^7$, together with the atoms to which they are attached, form one or more rings.

In certain embodiments, $R^5$ is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido.

In certain embodiments as discussed above, $R^5$ may be substituted by one or more substituents selected from substituted or unsubstituted alkyl alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $R^5$ is lower alkyl (e.g.,

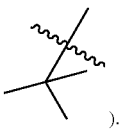

).

In certain embodiments, E is selected from

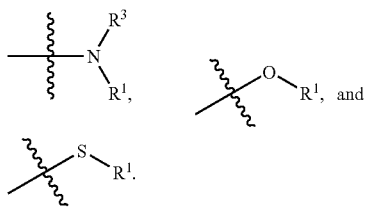

In certain such embodiments, Ar is selected from

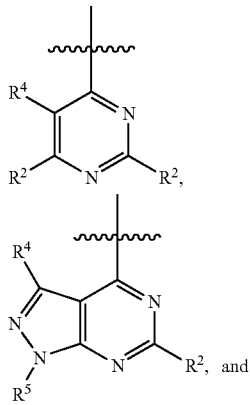

Definitions for such embodiments may be as those that are described above, including subcombinations of embodiments of E and Ar of narrower scope as set forth above.

For example, in certain embodiments, Ar is

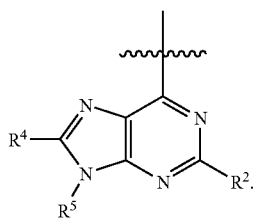

In certain such embodiments, E is

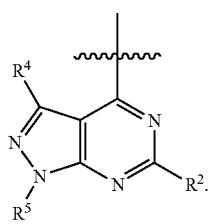

e.g., wherein, $R^1$ is selected from acrylyl (e.g.,

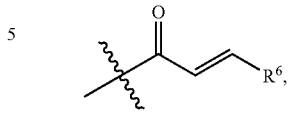

wherein $R^6$ is H) and substituted acetyl (e.g.,

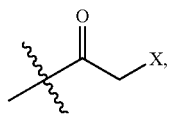

wherein X is Cl) and $R^3$ is selected from H and acrylyl (e.g.,

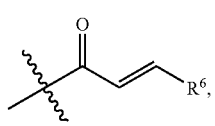

wherein $R^6$ is H). In certain such embodiments, $R^2$ is H, $R^4$ is aryl (e.g., phenyl, naphthyl), and $R^5$ is lower alkyl (e.g.,

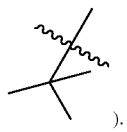

).

In certain embodiments, Ar is aryl (e.g.,

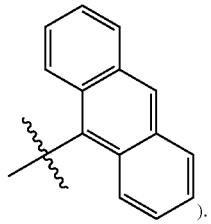 [SMILES: *c1c2ccccc2cc2ccccc12]

).

In certain such attachments, E and nitroalkenyl (e.g.,

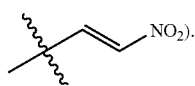

).

Exemplary compounds of Formula I include:

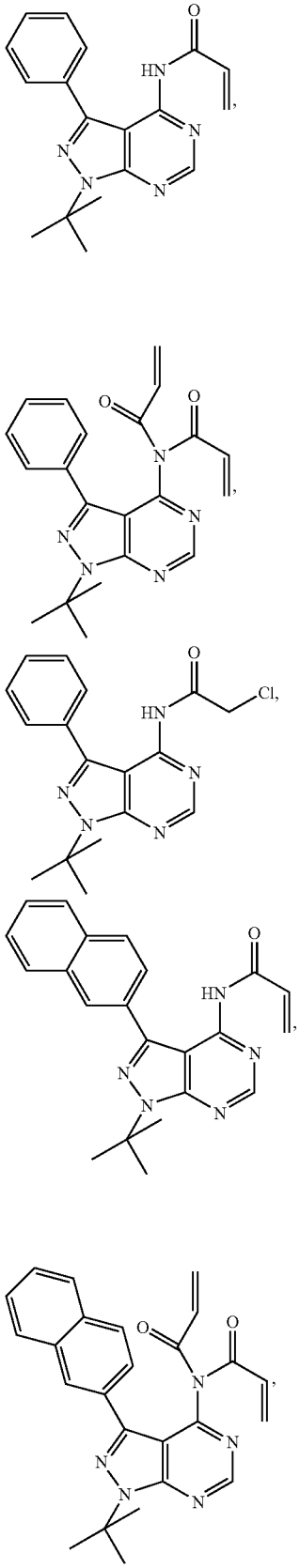

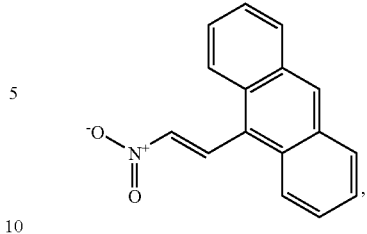

and salts (including pharmaceutically acceptable salts) of the foregoing.

In one aspect, the invention provides a pharmaceutical composition comprising a compound as disclosed herein and a pharmaceutically acceptable excipient or solvent.

BRIEF DESCRIPTION OF THE FIGURES

FIG. 3 shows an amino acid sqeuence alignment the Walker A motif in AAA ATPase and other ATPases.

DETAILED DESCRIPTION OF THE INVENTION

Overview

Figure 1:
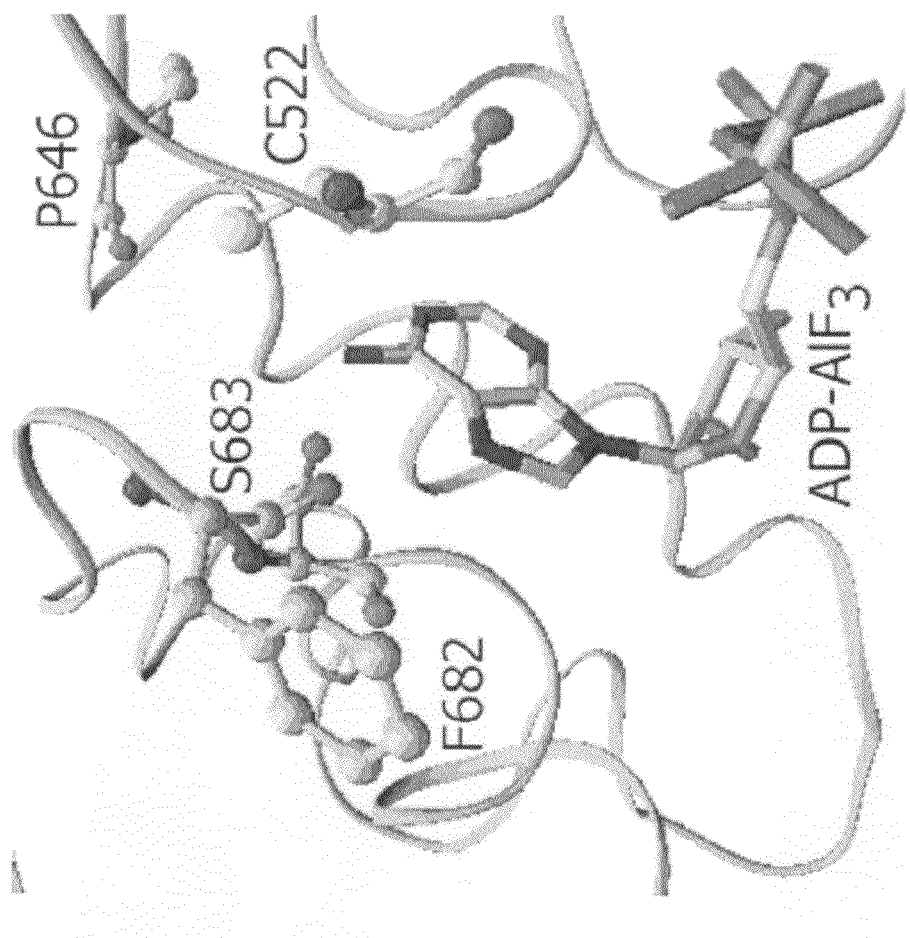
FIG. 1 shows the active site of p97 bound by ADP-AlF$_3$.

The invention provides compounds that inhibit p97, as well as methods to treat or prevent a disease or condition in a subject that would benefit by inhibition of p97.

In certain embodiments, the disclosure provides methods of inhibiting p97. Preferred inhibitors for use in the methods disclosed herein bind to the active site of p97, e.g., noncovalently or covalently. In certain such embodiments, the covalent binding may be reversible or irreversible. In certain embodiments, compounds useful in the subject methods may bind reversibly or irreversibly to a cysteine residue in the active site (e.g., Cys522). Without wishing to be bound by theory, exemplary compounds as disclosed herein have an acrylamide moiety that reacts with Cys522, consequently inhibiting the activity of p97.

Compounds

Compounds of the invention include compounds of Formula I as disclosed above. Such compounds are suitable for the compositions and methods disclosed herein. In other embodiments, the following compounds and their salts (including pharmaceutically acceptable salts) are compounds of the invention and are suitable for the compositions and methods disclosed herein:

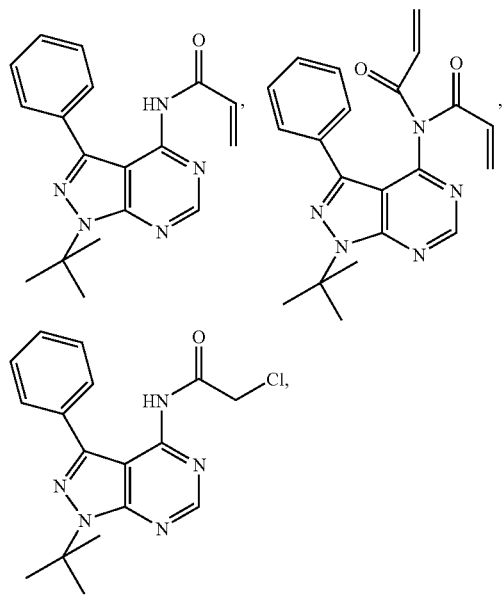

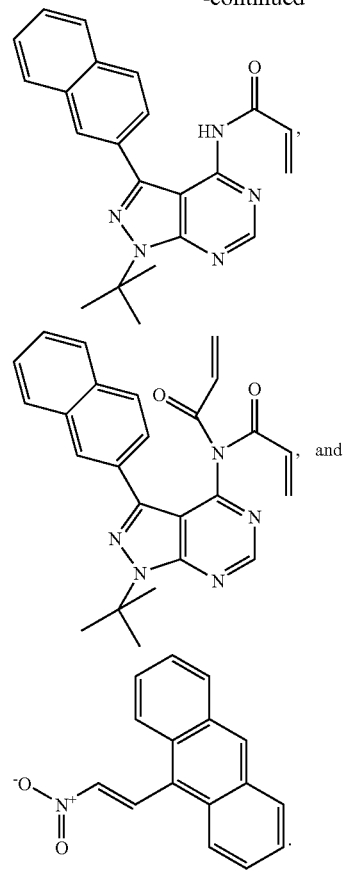

DEFINITIONS

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic" as used herein, includes straight, chained, branched or cyclic hydrocarbons which are completely saturated or contain one or more units of unsaturation. Aliphatic groups may be substituted or unsubstituted.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Examplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Examplary alkynyl groups include propynyl, butynyl, 3-methylpent-1-ynyl, and the like.

The term "amide", as used herein, refers to a group

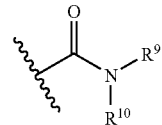

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

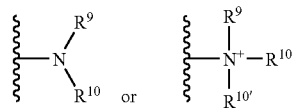

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "aryloxy", as used herein, refers to an aryl group having an oxygen attached thereto. Representative aryloxy groups include phenoxy, naphthoxyl, and the like.

The term "carbamate" is art-recognized and refers to a group

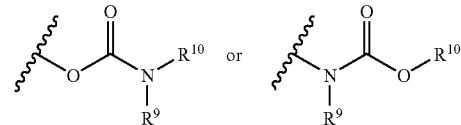

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group, such as an alkyl group.

The term "carboxy", as used herein, refers to a group represented by the formula-$CO_2H$.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester", as used herein, refers to a group —C(O)OR$^9$ wherein R$^9$ represents a hydrocarbyl group, such as an alkyl group or an aralkyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroaryloxy" refers to a heteroaryl group having an oxygen attached thereto. Representative heteroaryloxy groups include pyridoxy and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt or ester thereof.

The term "sulfonamide" is art-recognized and refers to the group represented by the general formulae

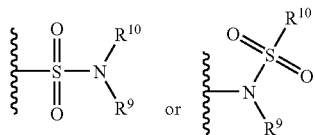

wherein $R^9$ and $R^{10}$ independently represents hydrogen or hydrocarbyl, such as alkyl.

The term "sulfoxide" is art-recognized and refers to the group —S(O)—$R^9$, wherein $R^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—$R^9$, wherein $R^9$ represents a hydrocarbyl, such as alkyl, aryl, or heteroaryl.

The term "thioalkyl", as used herein, refers to an alkyl group substituted with a thiol group.

The term "thioester", as used herein, refers to a group —C(O)S$R^9$ or —SC(O)$R^9$ wherein $R^9$ represents a hydrocarbyl, such as alkyl.

The term "thioether", as used herein, is equivalent to an ether, wherein the oxygen is replaced with a sulfur.

The term "urea" is art-recognized and may be represented by the general formula

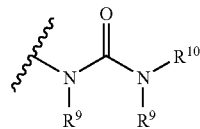

wherein $R^9$ and $R^{10}$ independently represent hydrogen or a hydrocarbyl, such as alkyl.

At various places in the present specification substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

As used herein, the term "inhibitor" is meant to describe a compound that blocks or reduces an activity of an enzyme (for example, inhibition of various activities of p97). An inhibitor can act with competitive, uncompetitive, or non-competitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal. In certain embodiments, a prodrug of a compound is an ester or amide of the compound. For example, a carboxylic acid residue of the compound can be converted to an amide or ester by techniques well known in the art, or, similarly, a hydroxyl or amine residue of the compound can be acylated.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, the term "treating" or "treatment" includes reversing, reducing, or arresting the symptoms, clinical signs, and underlying pathology of a condition in manner to improve or stabilize a subject's condition.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

Synthetic Preparation

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of Compounds can Involve the Protection and Deprotection of Various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the inhibitor. Such conjoint treatment may be achieved by way of the simultaneous, sequential, or separate dosing of the individual components of the treatment.

In certain embodiments, a compound of the invention is conjointly administered with one or more proteasome inhibitor(s).

In certain embodiments, a compound of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin, trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Treatment of Cancer

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer.

EXEMPLIFICATION

The following describes the preparation of representative compounds of the invention in greater detail. The following examples are offered for illustrative purposes, and are not intended to limit the invention in any manner. Those of skill in the art will readily recognize a variety of noncritical parameters which can be changed or modified to yield essentially the same results.

Example 1

Structure Based Drug Design to Develop a Covalent Inhibitor of p97

Figure 2:
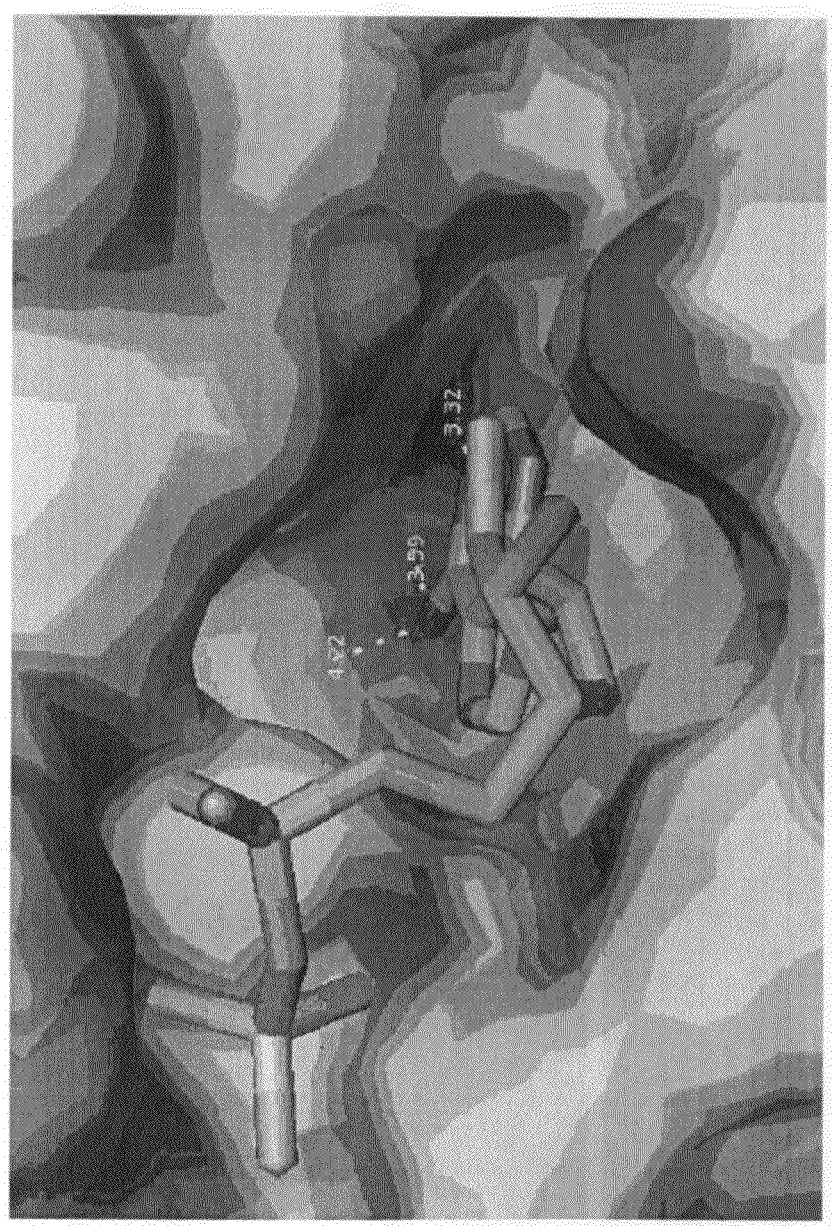
FIG. 2 shows a different perspective from FIG. 1 of active site of p97 bound by ADP-AlF$_3$.

The D2 ATPase domain of p97 has a cysteine residue at position 522, the side chain of which projects into the active site nearby the amino ($NH_2$) group attached at the C6 position of the purine of bound ADP-aluminum fluoride complex (DeLaBarre, B. et al. *Nat. Struct. Biol.* (2003) 10, 856-863; see FIG. 1 and FIG. 2). An ATP analog carrying an electrophilic substitution at C6 may react with this cysteine residue and inactivate p97. Notably, a cysteine at position 522 is not essential for p97 ATPase activity. For example, the budding yeast ortholog of p97, Cdc48, does not have a cysteine in this position (FIG. 3). Indeed, the presence of cysteine at this position in members of the AAA ATPase family is variable: the D1 domain of NEM-sensitive factor (NSF) has a cysteine in the equivalent position, whereas five of the six AAA ATPase subunits of the 26S proteasome do not.

To develop an inhibitor capable of reacting with this cysteine, scaffolds were derivitized in a variety of ways. For example, a purine scaffold was derivatized with various electrophilic groups were attached to the C6 position as shown below, including Michael acceptors (compounds 2, 3, 6 and 7), and a chloracetamide (compound 4). As negative controls, compounds were prepared that retained an amino group attached at C6 (compounds 1 and 5).

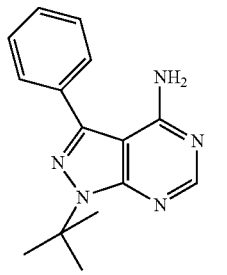

1

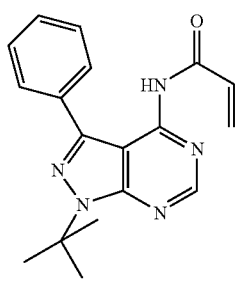

2

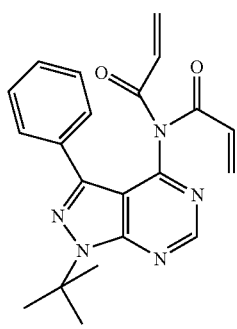

3

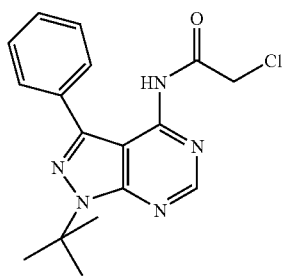

4

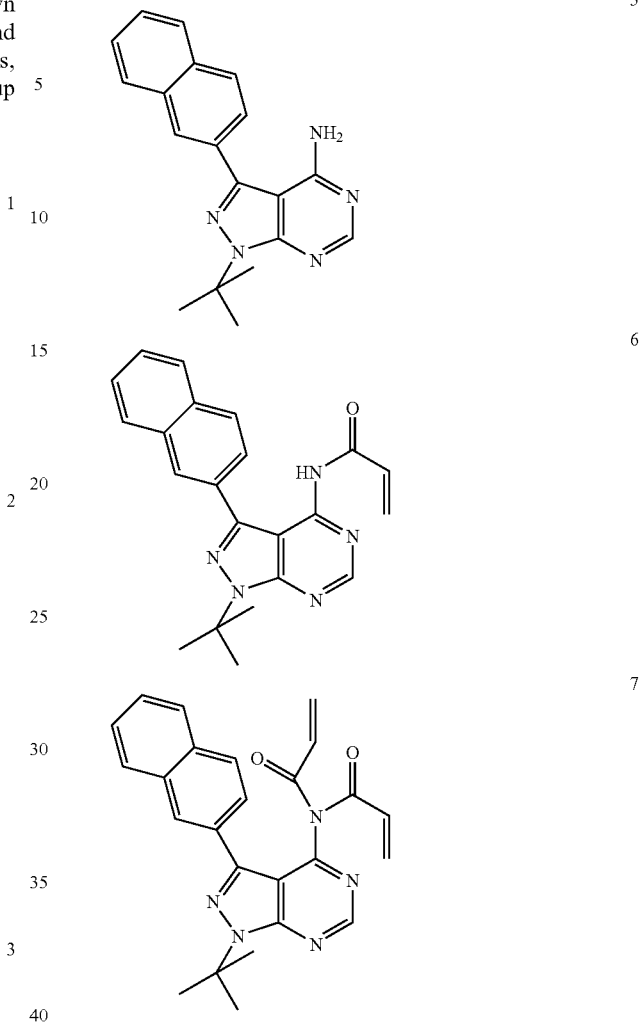

Figure 4:
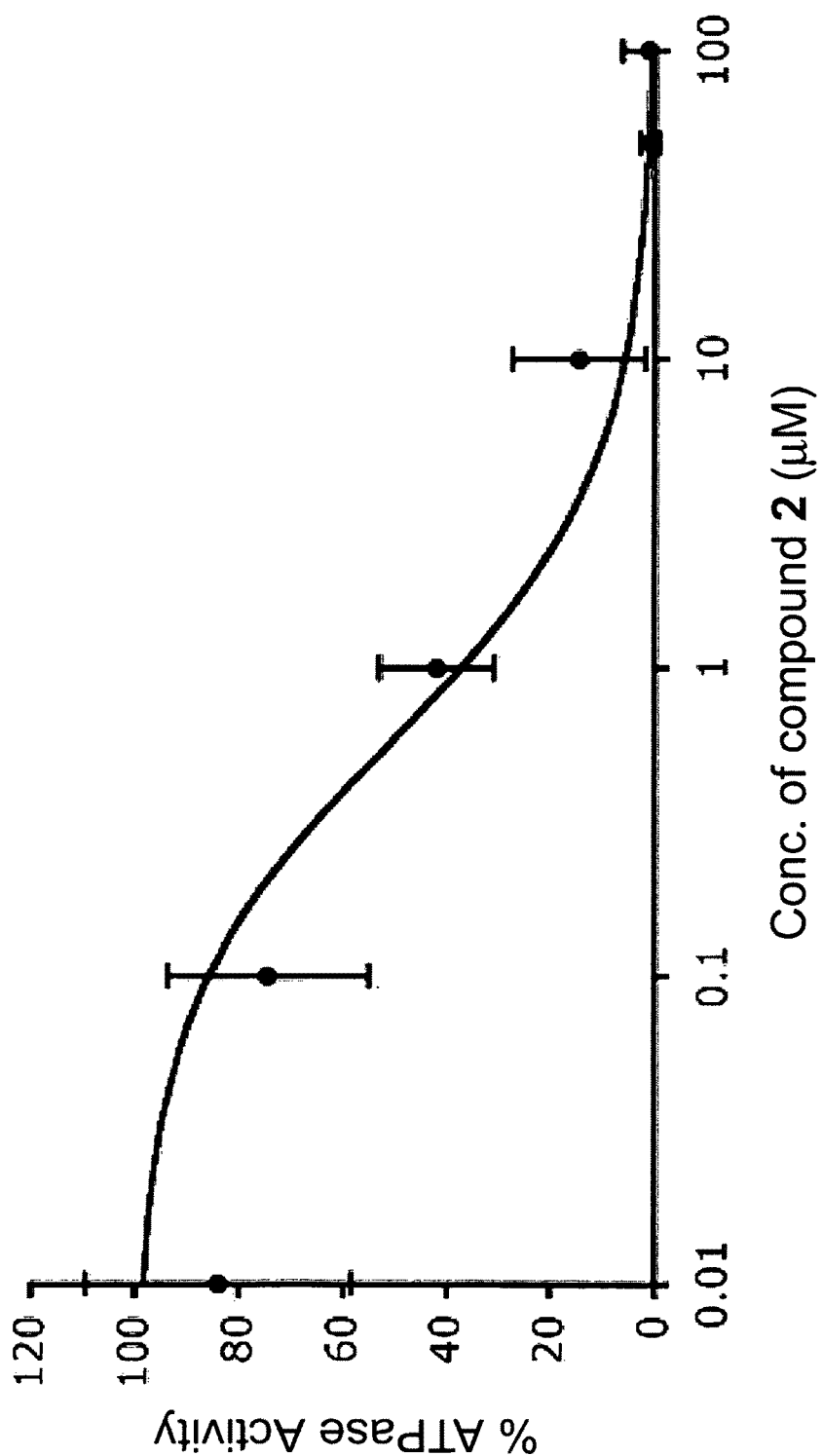
FIG. 4 shows a histogram of ATPase activity upon treatment with compound 2.

Compounds were tested for their ability to inhibit the ATPase activity of purified wild type murine p97 and T532C-Cdc48, a mutant of yeast Cdc48 in which the residue analogous to cysteine 522, threonine 532, was converted to cysteine. Compounds were individually preincubated at various concentrations with 200 nM p97 for 20 min at 23° C., after which ATP was added and ATPase activity was measured using the malachite green assay method (Lanzetta, P. A. et al. *Anal. Biochem.* (1979) 100, 95-97) to determine the amount of compound required to achieve 50% inhibition ($IC_{50}$). All compounds demonstrated inhibitory activity in this assay, except for the control compounds 1 and 5 (see Table 1). The most potent inhibitor was compound 2, which contains a phenyl substituent at C7 and a single Michael acceptor at C6 (see FIG. 4).

TABLE 1

| | In vitro ATP Hydrolysis Activity | |
|---|---|---|
| | $IC_{50}$ (μM) of Enzyme | |
| Compound | WT-mP97 | T532C-Cdc48 |
| 1 | >100 | >100 |
| 2 | 0.6 ± 0.2 | 14 ± 5 |
| 3 | 1.1 ± 0.7 | 26 ± 6 |

TABLE 1-continued

In vitro ATP Hydrolysis Activity

| | $IC_{50}$ (μM) of Enzyme | |
|---|---|---|
| Compound | WT-mP97 | T532C-Cdc48 |
| 4 | 4.5 ± 3.5 | 35 ± 8 |
| 5 | >100 | >100 |
| 6 | 3 ± 1 | 24 ± 7 |
| 7 | 1.3 ± 0.7 | 22 ± 11 |

Figure 5:
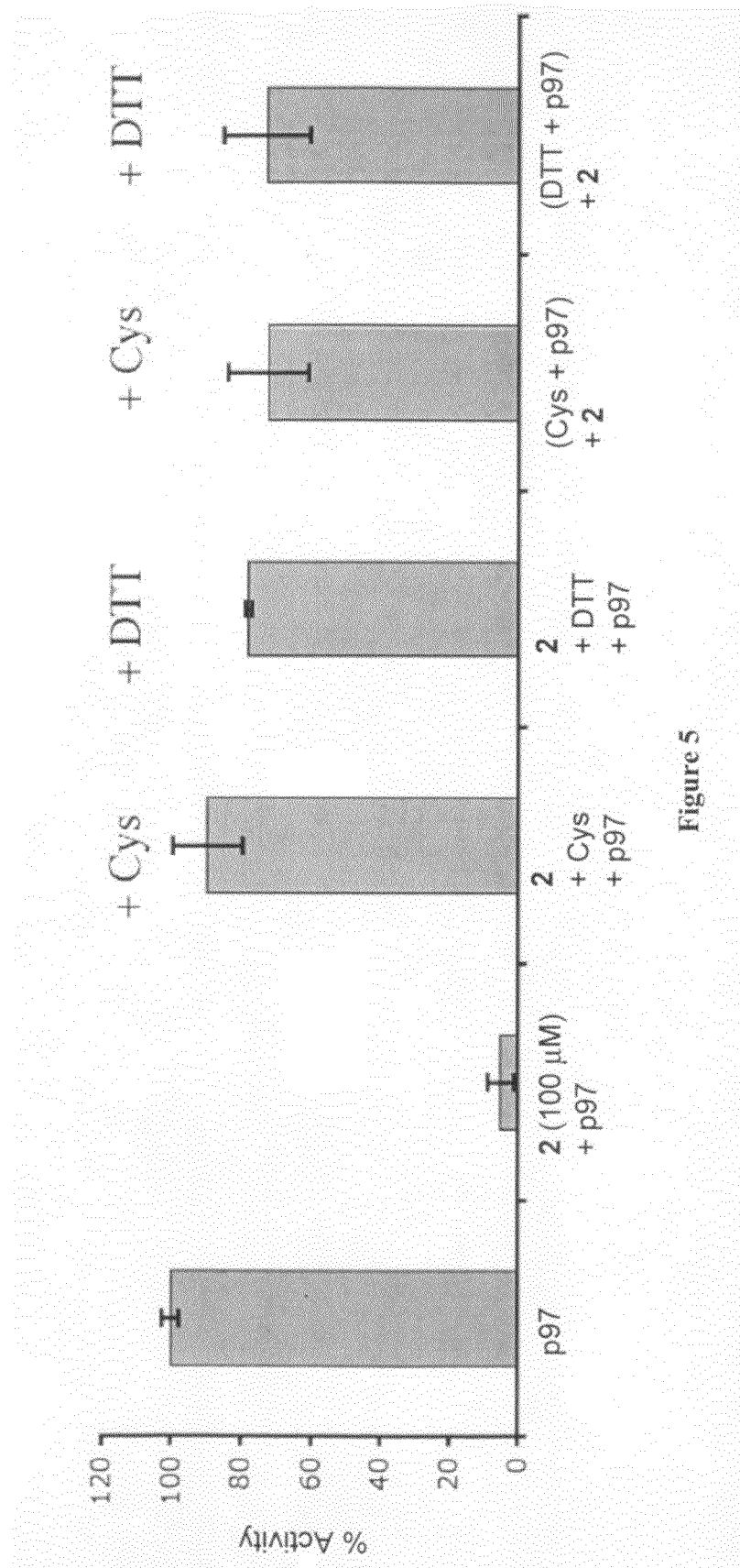
FIG. 5 shows a histogram of ATPase activity.
Figure 6:
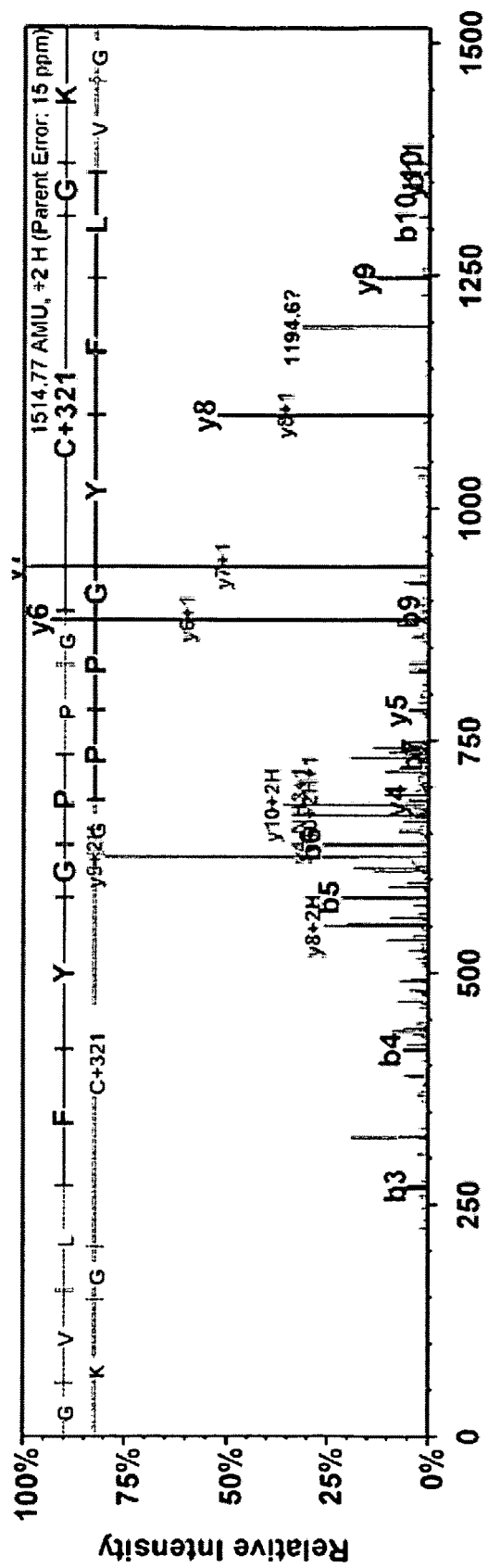
FIG. 6 shows results from a mass spectrum.

To determine if inhibition by compound 2 requires a reactive thiol, the experiment was repeated with p97 except that various nucelophiles were included during the preincubation. The data in FIG. 5 demonstrate that the inhibitory effect of compound 2 can be counteracted by inclusion of either cysteine or dithiothreitol in the preincubation buffer. To evaluate whether compound 2 modifies cysteine 522, inhibited p97 was digested with trypsin and peptides were fractionated by HPLC and analyzed by tandem mass spectrometry. The data shown in FIG. 6 confirm that compound 2 formed a covalent adduct on cysteine 522.

To determine whether cysteine 522 is necessary for inhibition of p97 by compound 2, a mutant of p97 was constructed in which cysteine 522 was converted to either alanine (C522A-mp97) or threonine (C522T-mp97). The $IC_{50}$ values of compound 2 were measured the against various enzymes during a 20-minute preincubation (see Table 2). Mutation of cysteine 522 in p97 to either alanine or threonine decreased sensitivity to compound 2 by greater than 100-fold. On the other hand, yeast Cdc48, which normally is quite resistant to compound 2, became nearly 30-fold more sensitive to the compound upon introduction of a cysteine in place of threonine 532. Together, these data indicate that a cysteine at position 522 is both necessary and sufficient to confer sensitivity to compound 2.

TABLE 2

In vitro ATP Hydrolysis Activity

| Enzyme | $IC_{50}$ (μM) |
|---|---|
| WT-mp97 | 0.62 ± 0.25 |
| C522A-mp97 | 110 ± 33 |
| C522T-mp97 | 82 ± 45 |
| Yeast Cdc48 | 376 ± 95 |
| T532C-yeast Cdc48 | 14 ± 5 |
| Hamster NSF | 105 ± 31 |
| Human 19S ATPase* | 75 ± 19 |

*Human Rpt3 contains a cysteine in Walker A motif.

To further address the specificity of inhibition by compound 2, its activity against two other AAA ATPases, NSF and the 26S proteasome, was assayed. Although NSF is known to be sensitive to thiol-reactive agents, it was more than 100-fold less sensitive to compound 2 than p97 (Table 2). Likewise, inhibition of ATP hydrolysis by human 19S ATPase of the 26S proteasome was observed only at high concentrations of compound 2 ($IC_{50}$=75 μM; Table 2). The results with NSF and the 26S proteasome are noteworthy because both the active D1 domain of NSF and the Rpt3 subunit of the 26S proteasome have a cysteine in the position analogous to cysteine 522 of p97 (FIG. 3).

Figure 7:
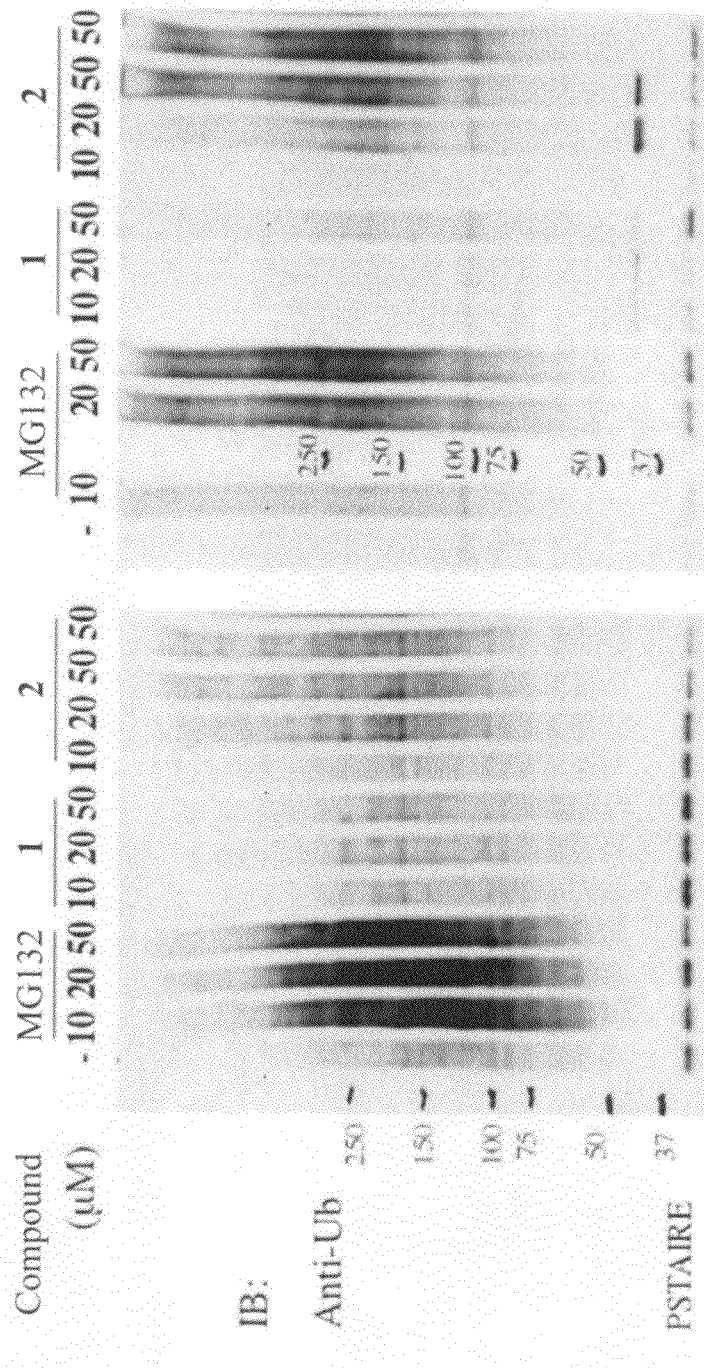
FIG. 7 shows results from a Western blot.
Figure 8:
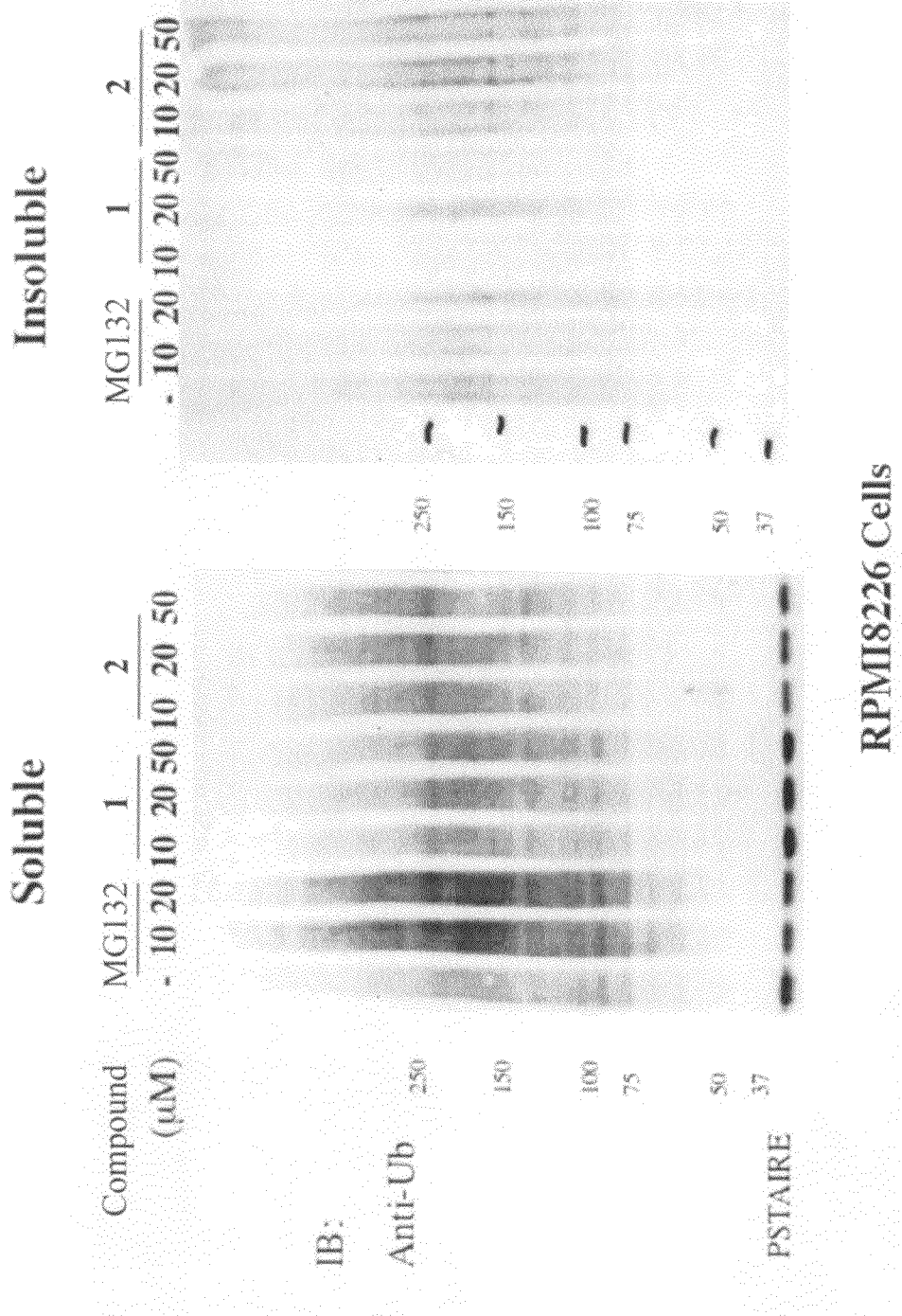
FIG. 8 shows results from a Western blot.
Figure 9:
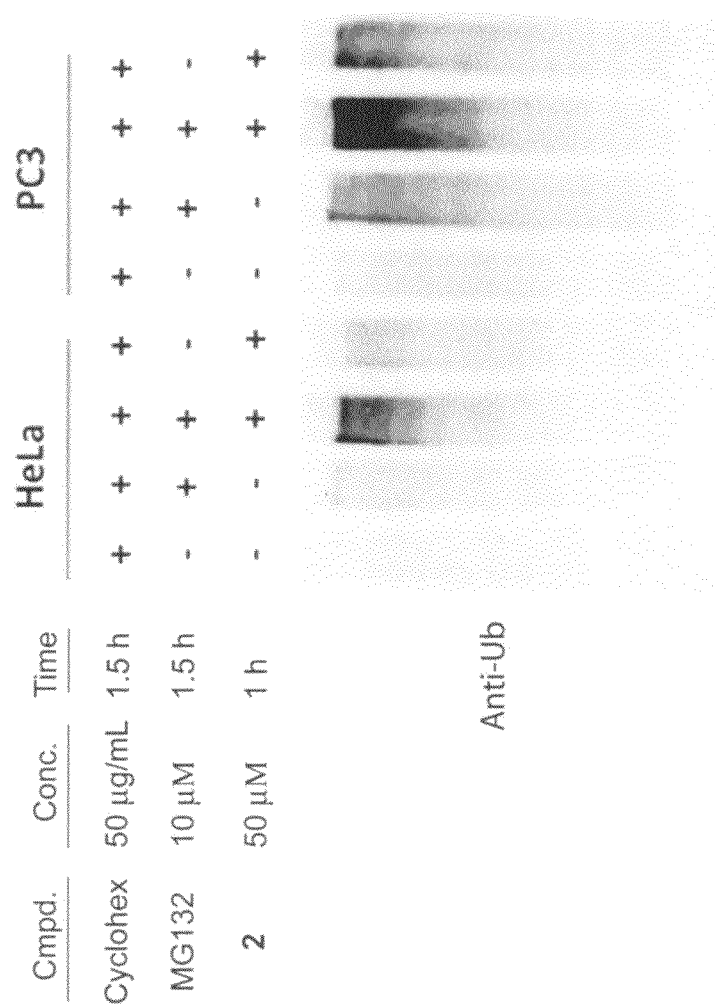
FIG. 9 shows results from a Western blot.
Figure 10:
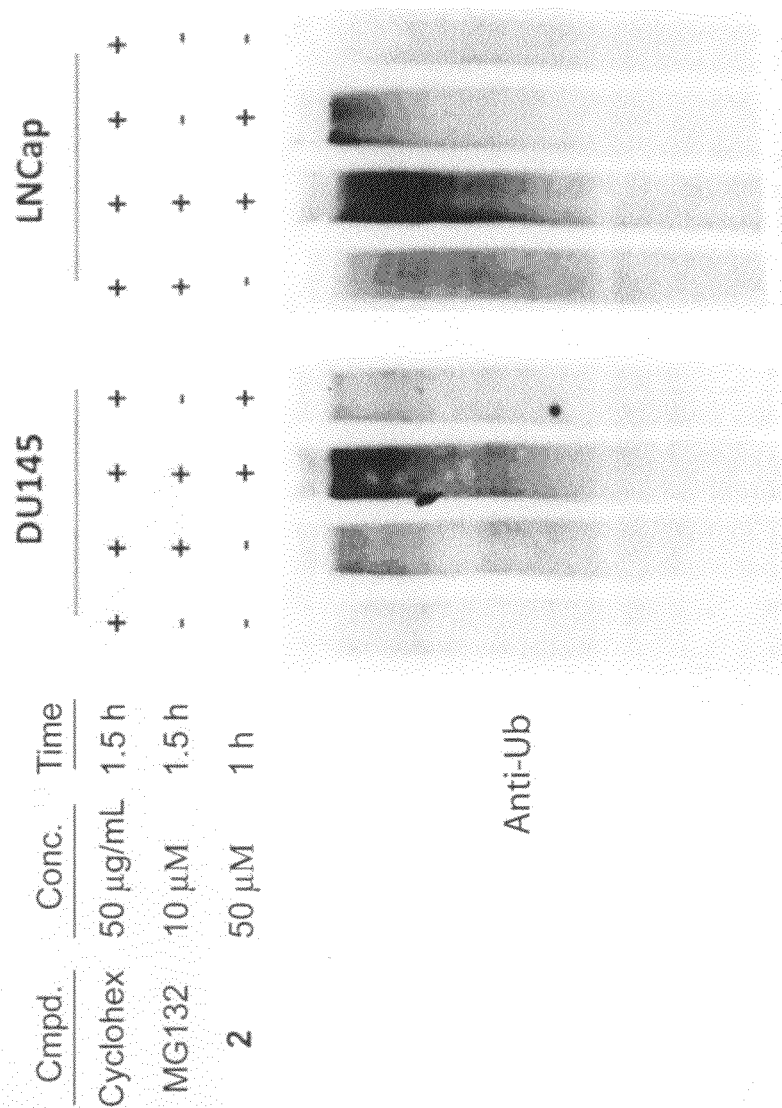
FIG. 10 shows results from a Western blot.

To evaluate whether compound 2 can target p97 activity in cells, we sought to determine whether this compound induces accumulation of high molecular weight ubiquitin conjugates, since it is known that RNAi-mediated knockdown of p97 in mammalian cells has this effect (Wojcik, C. et al. *J. Cell Sci.* (2004) 117, 281-292). As a positive control for this experiment, the proteasome inhibitor MG132 was used. HeLa or RPM18226 cells were treated for 60 minutes at 37° C. with 10, 20, or 50 μM of MG132, compound 2, or the inactive compound 1 that lacks the Michael acceptor. The cells were then harvested, lysed, and centrifuged to generate soluble and insoluble fractions. These fractions were then immunoblotted with anti-ubiquitin antibodies to detect accumulation of high molecular weight conjugates. Blots were also probed with anti-PSTAIRE antibodies as a loading control. The data shown in FIG. 7 (HeLa cells) and FIG. 8 (RPMI8226 cells) reveal that compound 2, but not its inactive analog compound 1, caused accumulation of high molecular weight ubiquitin conjugates. This effect is particularly pronounced in the insoluble fraction. Moreover, co-treatment of compound 2 with MG132 in the presence of a protein synthesis inhibitor, cycloheximide, caused more accumulation of ubiquitin conjugates in HeLa and PC3 (FIG. 9) and DU145 and LNCaP (FIG. 10) cell lines.

Figure 11:
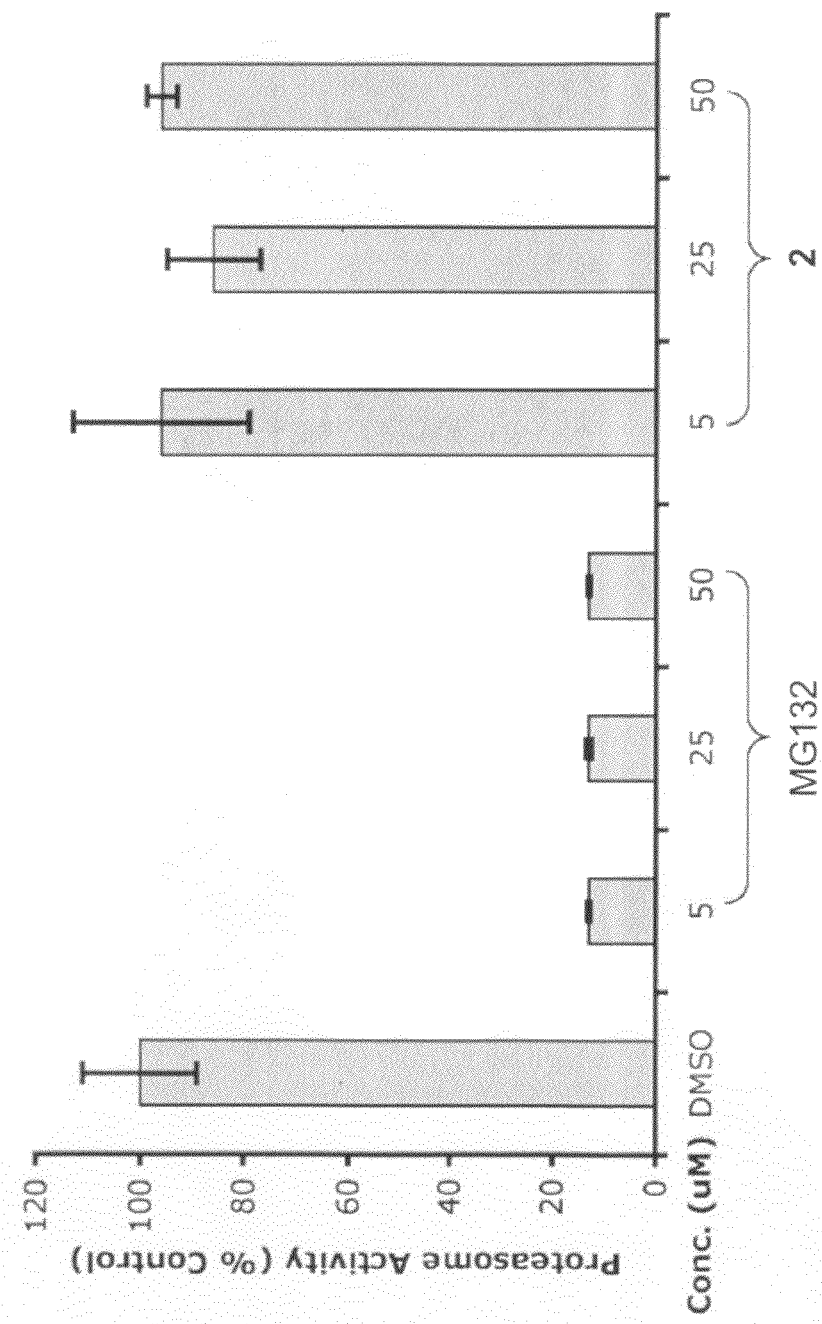
FIG. 11 shows a histograph of proteasome activity in the presence of MG132 or compound 2.

The effects of compound 2 on ubiquitin conjugate accumulation are not due to inhibition of the proteasome, because it was shown that compound 2 synergizes with a proteasome inhibitor and compound 2 does not inhibit hydrolysis of a proteasome substrate, LLVY-AMC, in vitro (FIG. 11) Human 26S proteasome complex was affinity purified from HEK293 cells that stably express tagged human Rpn 11 as described (Wang et al. *Biochemistry* (2007) 46, 3553-3565). Purified human 26S proteasome (19 nM) was incubated with either DMSO, MG132 or compound 2 for 30 min at room temperature and fluorogenic proteasome substrate LLVY-AMC (60 μM) was added to initiate the reaction. Fluorescence intensity was monitored every 3 min over 30 min.

Figure 12:
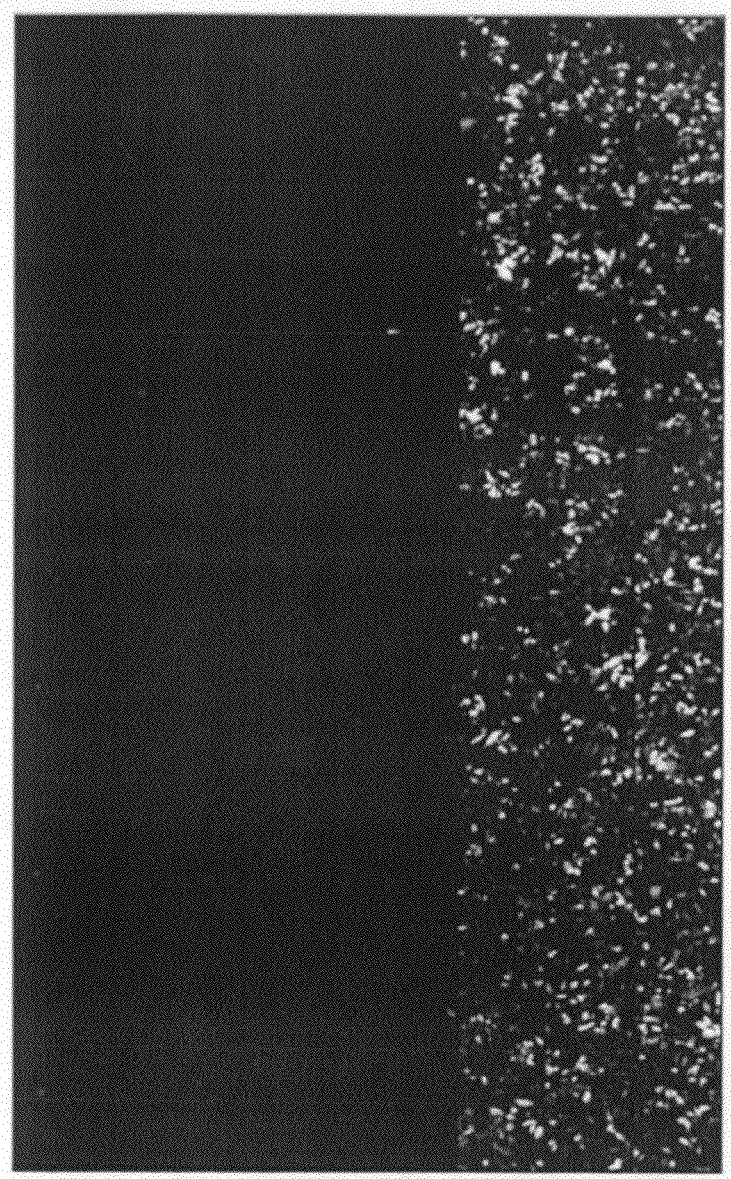
FIG. 12 shows images of HeLa cells expressing Ub$_{G76V}$-GFP that were treated with the indicated concentration of siRNA that target the indicated gene. Luci refers to Luciferase.
Figure 13:
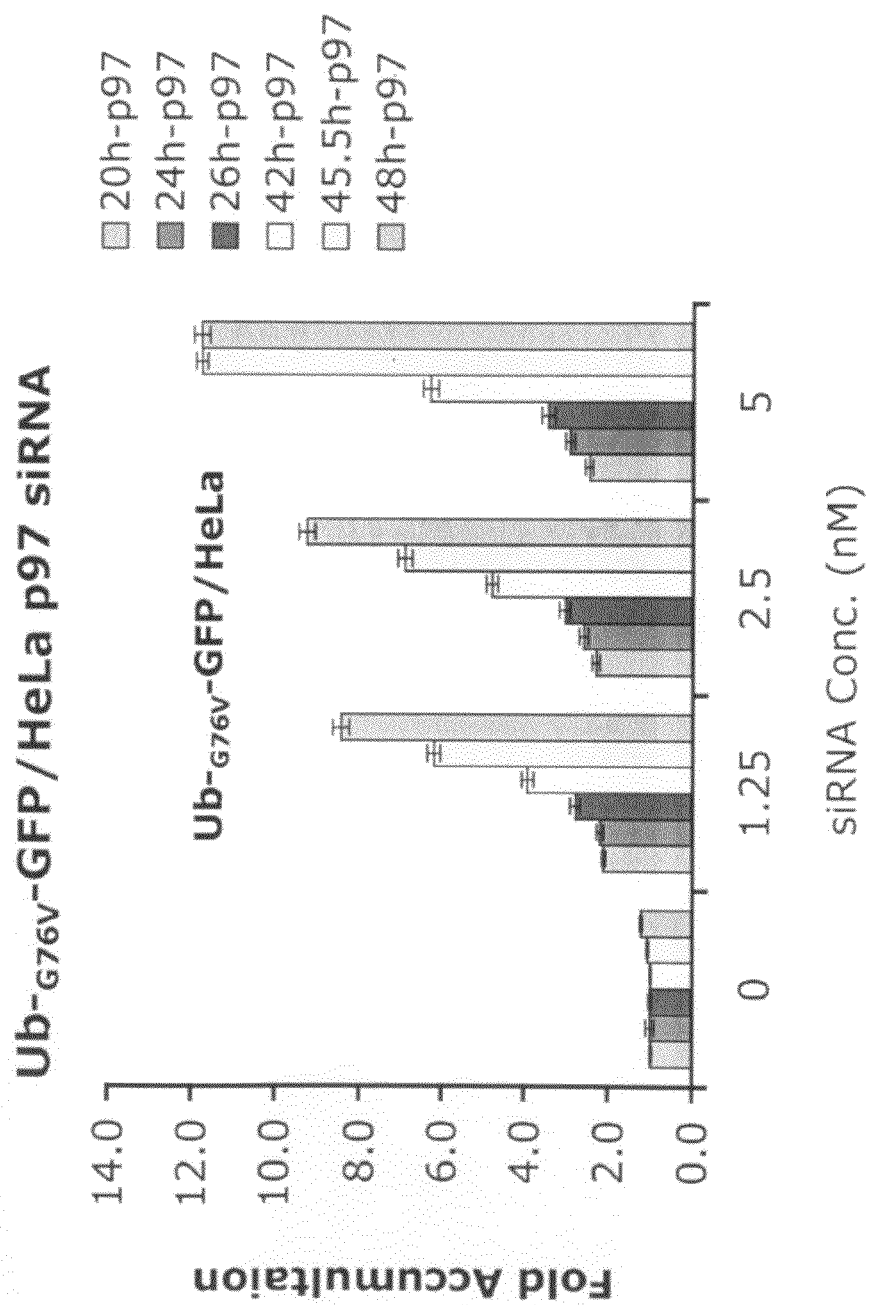
FIG. 13 shows a histogram of accumulation of Ub$_{G76V}$-GFP.
Figure 14:
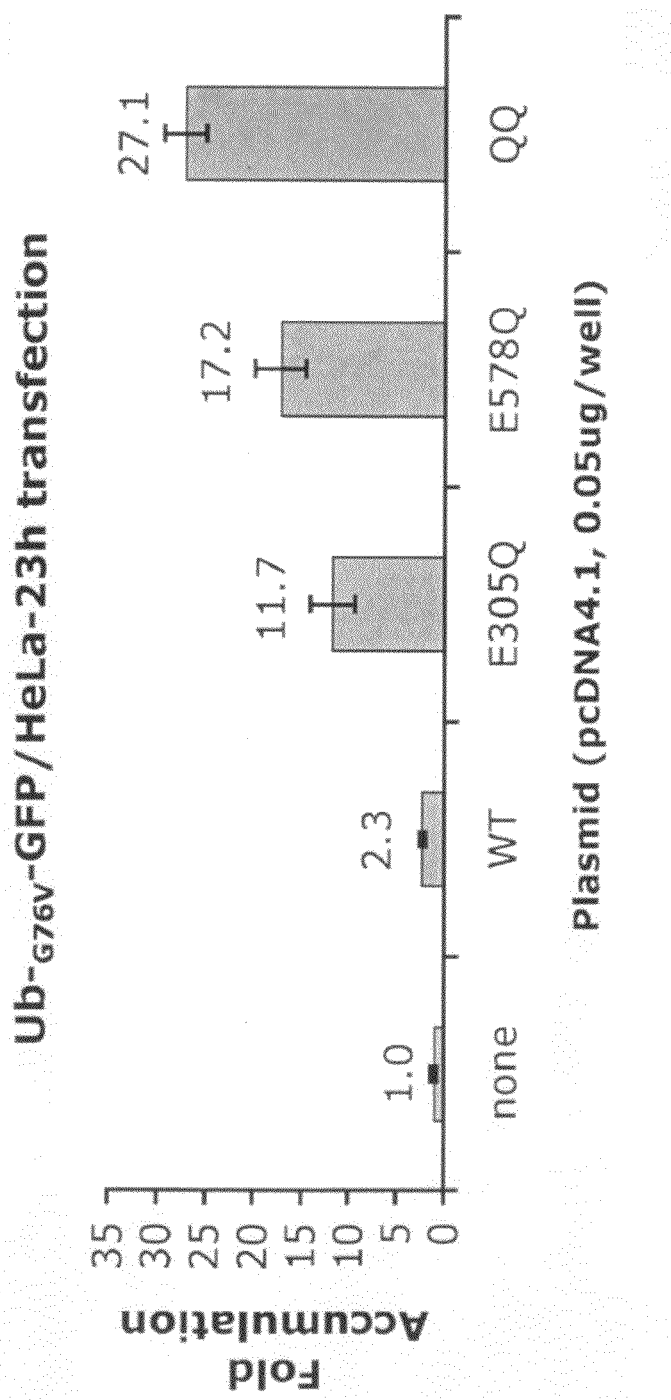
FIG. 14 shows a histogram of accumulation of Ub$_{G76V}$-GFP.
Figure 15:
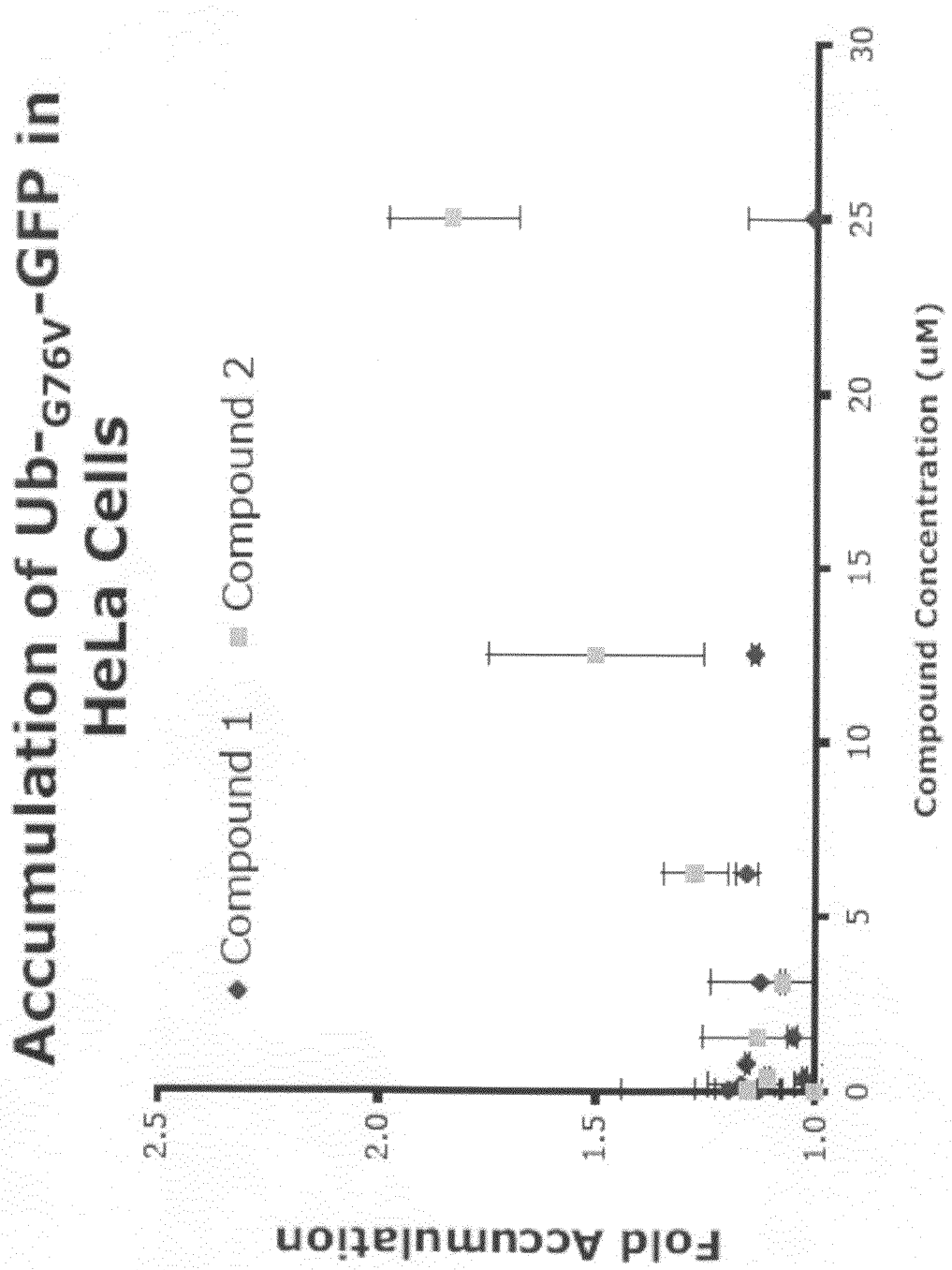
FIG. 15 shows a histogram of accumulation of Ub$_{G76V}$-GFP.
Figure 16:
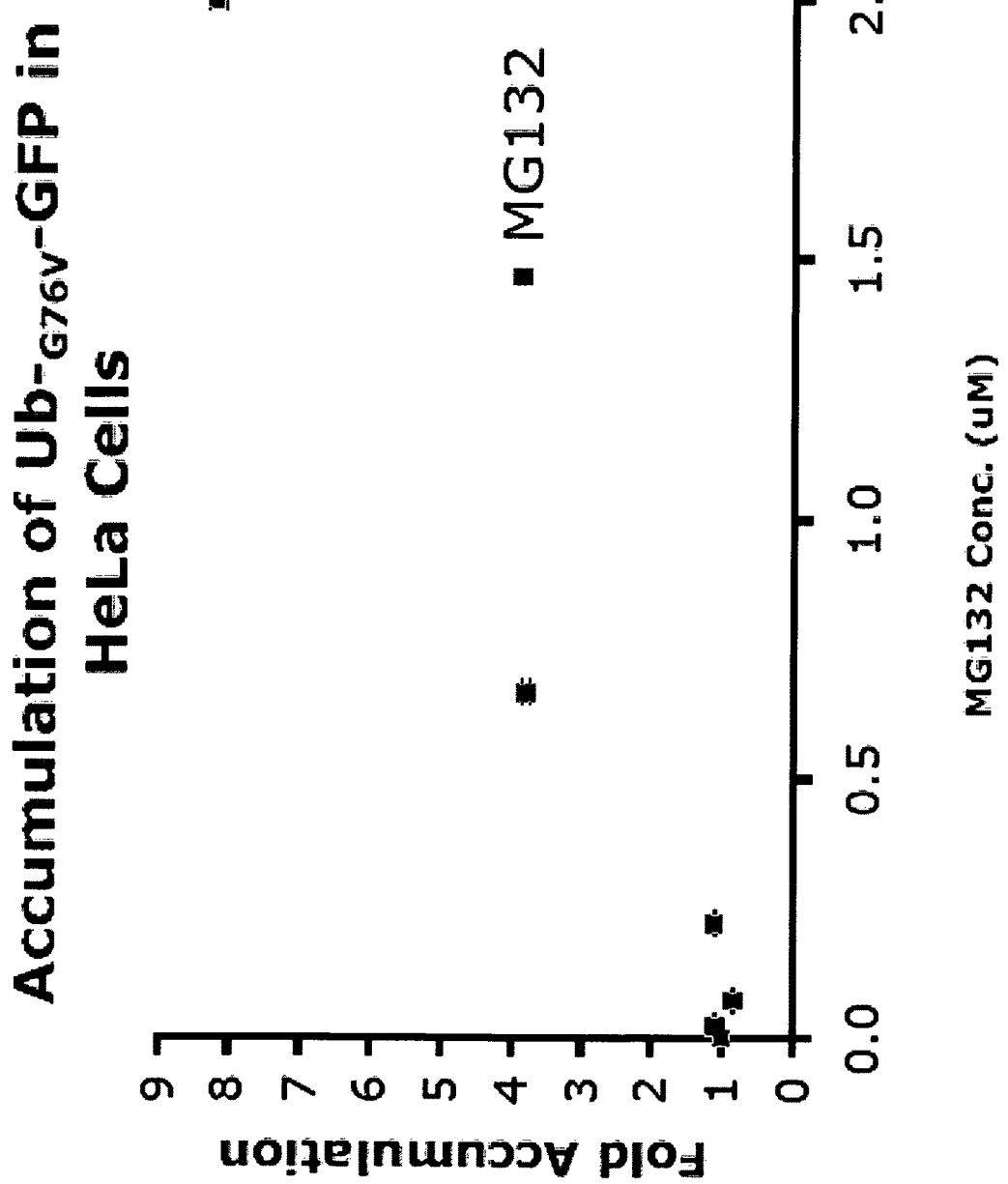
FIG. 16 shows a histogram of accumulation of Ub$_{G76V}$-GFP.

As a second test of whether compound 2 can inhibit p97 in vivo, it was evaluated whether 2 can cause accumulation of the normally unstable protein $Ub_{G76V}$-GFP, which has been shown to accumulate in cells in which p97 has been depleted by siRNA (see FIG. 12 and FIG. 13; see Wojcik, C. et al. *Mol. Biol. Cell* (2006) 17, 4606-4618) or in cells that express a dominant-negative version of p97 (FIG. 14). A HeLa cell line that stably expresses $Ub_{G76V}$-GFP was treated with either compound 2 or the inactive compound 1 for 4 hours at 37° C., and was then evaluated by fluorescence microscopy. As a control, the same cells were treated with the proteasome inhibitor MG132. In the latter set of experiments, a HeLa cell line that stably expresses $Ub_{G76V}$-GFP was transfected with either wild type (WT), D1 mutant (E305Q), D2 mutant (E578Q) or E305Q, E578Q double mutant (QQ) murine 97-pcDNA4.1 plasmid (0.05 μg/100 μL) in a 96-well plate. After 23 h, the intensity of $Ub_{G76V}$-GFP signal was measured on a Molecular Devices ImageXpress automated fluorescence microscope. These results provide evidence that p97 ATPase activity is required for the proper turnover of $Ub_{G76V}$-GFP in HeLa cells. Both MG132 (see FIG. 15) and compound 2, but not compound 1 (see FIG. 16), caused accumulation of $Ub_{G76V}$-GFP. The direct accumulation of Ub-$_{G76V}$-GFP caused by compound 2 at 25 μM is 4-fold less than that caused by MG132 at 2 μM. This is likely due to the fact that only fully folded Ub-$_{G76V}$-GFP should require p97 for degradation by the proteasome.

Figure 17:
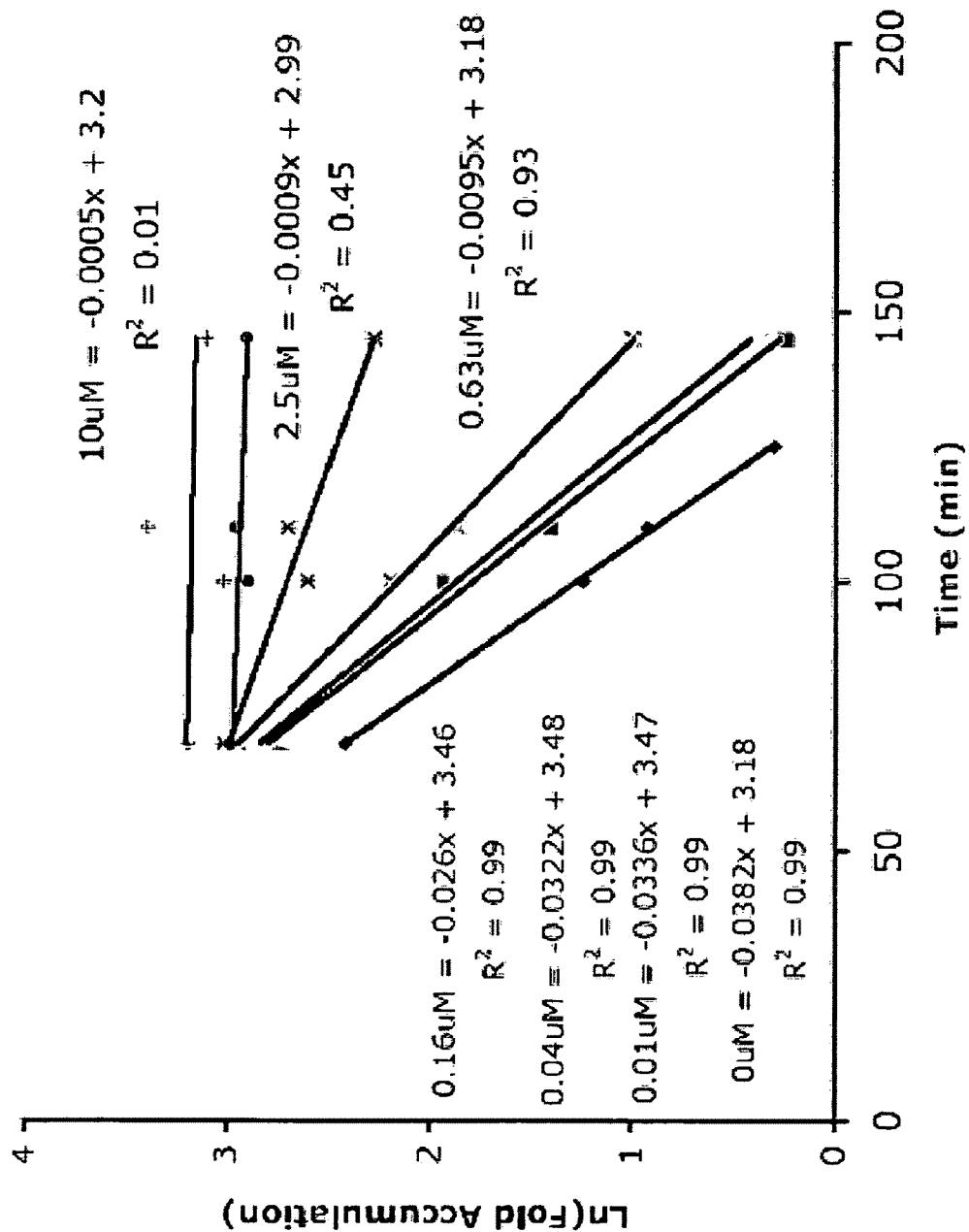
FIG. 17 shows a histogram of the rate of loss of accumulation of Ub$_{G76V}$-GFP in cells treated with MG132.
Figure 18:
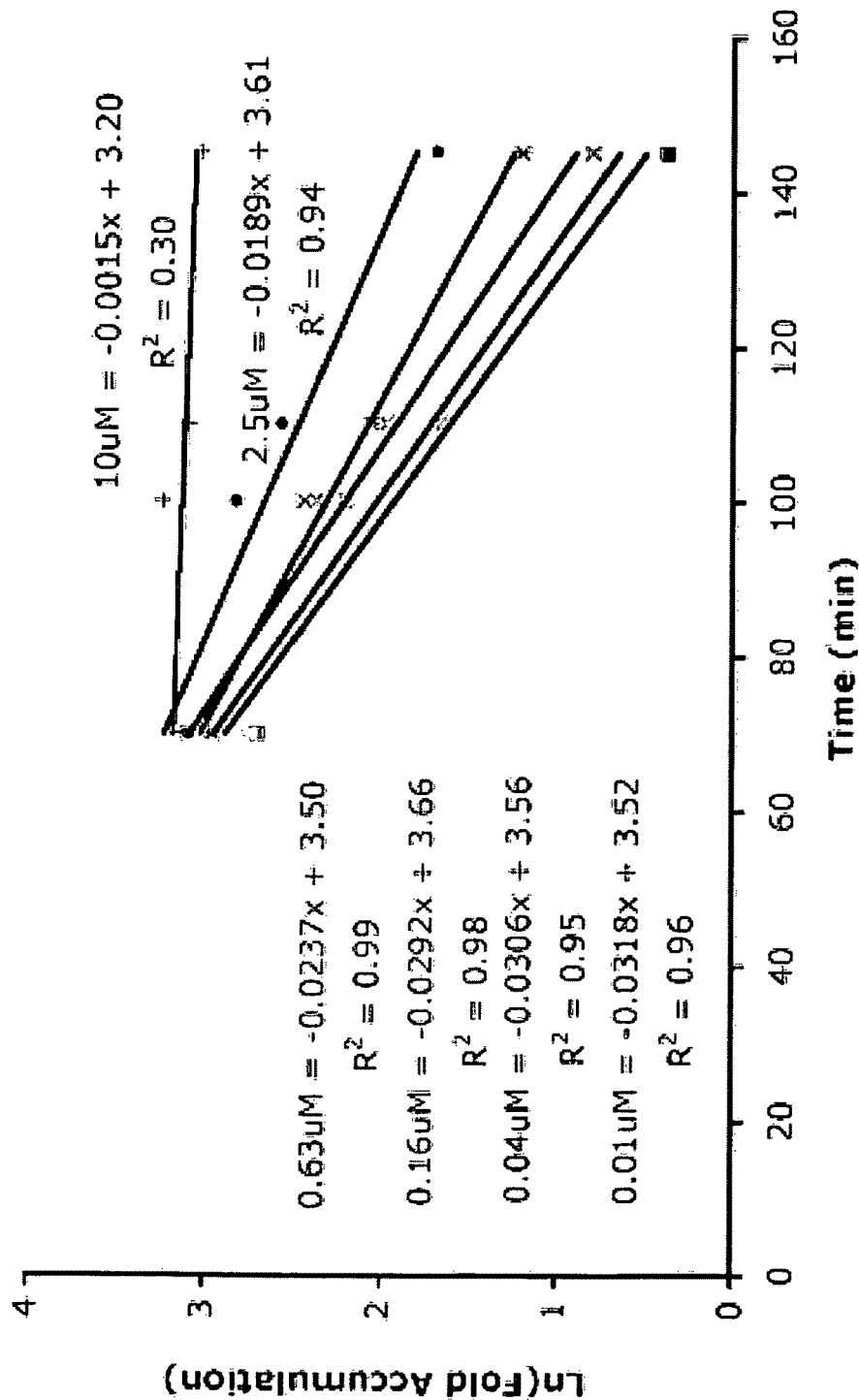
FIG. 18 shows a histogram of the rate of loss of accumulation of Ub$_{G76V}$-GFP in cells treated with compound 2.

To evaluate this possibility, an assay was developed to determine the rate of degradation of pre-accumulated Ub-$_{G76V}$-GFP molecules. Ub-$_{G76V}$-GFP/HeLa cells were treated with MG132 (2 μM) for 1 h, during which time Ub-$_{G76V}$-GFP is synthesized and may fold into its active (fluorescent) conformation. Cells were then washed with PBS three times remove the MG132. Cells were then refreshed by adding DMEM containing cycloheximide (50 µg/mL; to block production of more Ub-$_{G76V}$-GFP) and test compounds (0~10 µM) were added into cells. Eight 96-well plates were prepared and one of the plates was imaged at 25, 50, 70, 100, 110, 125, 145, or 170 min after washing with PBS three times. After washing out MG132, degradation of pre-accumulated Ub-$_{G76V}$-GFP appears to follow pseudo-first order reaction. Rate constant (K; 1/min) can be determined from the slope of plotting Ln (Fold Accumulation) versus Time (min) (see FIG. 17 and FIG. 18). Half-lives of pre-accumulated Ub-$_{G76V}$-GFP can be calculated by Ln2/K. IC$_{50}$ values of MG132 and compound 2 on the decay of Ub-$_{G76V}$-GFP measured by this method were calculated to be 0.24±0.04 µM (Table 3) and 1.25±0.47 µM (Table 4), respectively. Compound 1 showed no effect up to 10 µM.

TABLE 3

Inhibition of Ub-$_{G76V}$-GFP degradation by MG132.

| Conc. MG132 (µM) | K (1/min) | t$_{1/2}$ (min) = Ln(2)/k | % K |
|---|---|---|---|
| 0 | 0.0382 | 18 | 100 |
| 0.01 | 0.0336 | 21 | 88 |
| 0.04 | 0.0322 | 22 | 84 |
| 0.16 | 0.0260 | 27 | 68 |
| 0.63 | 0.0095 | 73 | 25 |
| 2.5 | 0.0005 | 1386 | 1 |
| 10 | 0.0009 | 770 | 2 |

IC$_{50}$ = 0.24 ± 0.04 µM

TABLE 4

Inhibition of Ub-$_{G76V}$-GFP degradation by compound 2.

| Conc. Cmpd. 1 (µM) | K (1/min) | t$_{1/2}$ (min) = Ln(2)/k | % K |
|---|---|---|---|
| 0 | 0.038 | 18 | 100 |
| 0.01 | 0.0318 | 22 | 83 |
| 0.04 | 0.0306 | 23 | 80 |
| 0.16 | 0.0292 | 24 | 76 |
| 0.63 | 0.0237 | 29 | 62 |
| 2.5 | 0.0189 | 37 | 49 |
| 10 | 0.0015 | 462 | 4 |

IC$_{50}$ = 1.25 ± 0.47 µM

Figure 19:
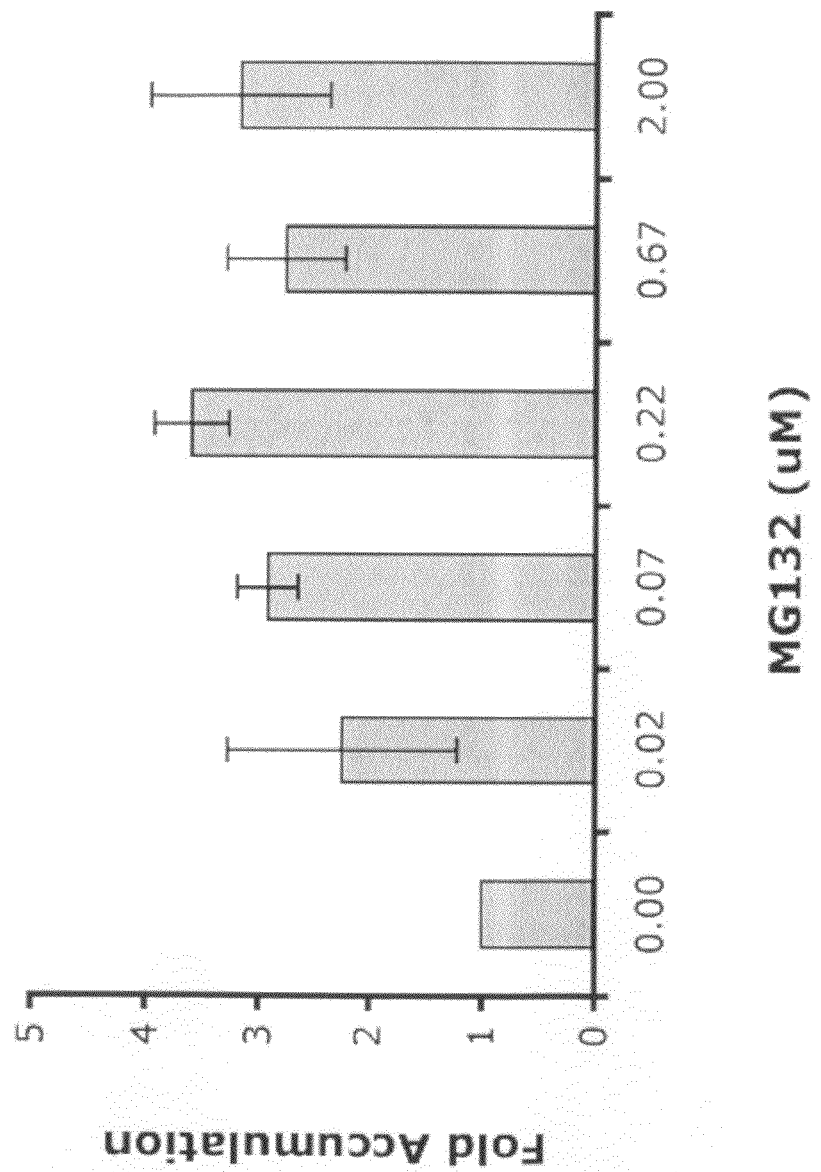
FIG. 19 shows a histogram of accumulation of TCR-alpha-GFP.
Figure 20:
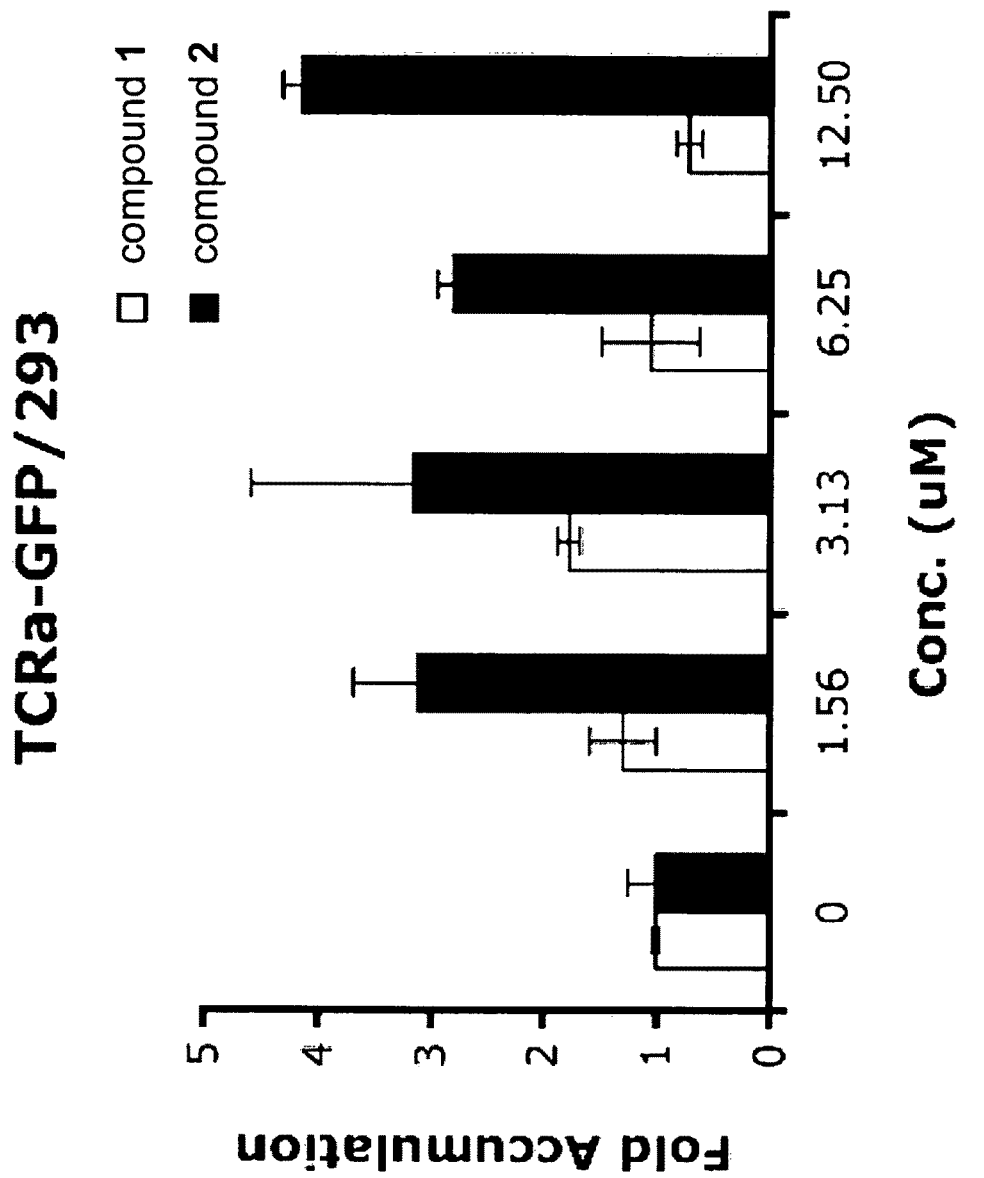
FIG. 20 shows a histogram of accumulation of TCR-alpha-GFP.

Since p97 has a well-established role in ERAD, it was also determined whether compound 2 affects the accumulation of an ERAD-reporter, TCR-alpha-GFP. HEK293 cells that stably expressed TCR-GFP were treated with MG132 (see FIG. 19), compound 1 or compound 2 (FIG. 20) at the indicated concentrations for 2 h at 37° C. prior to being imaged by fluorescence microscopy to determine TCR-GFP accumulation. Compound 2 clearly provoked substantial TCR-alpha-GFP accumulation (FIG. 20). It was thus concluded that compound 2 inhibits p97 in cells, resulting in the accumulation of both soluble and insoluble high molecular weight ubiquitin conjugates and UPS substrates whose degradation depends upon p97.

To probe further the effect of compound 2 and related compounds 1, 3, 5, 6 and 7, various concentrations of these compounds were added to 13 different cell lines and incubated for 48 or 72 h. An MTT assay was then performed to evaluate cell growth and survival. IG$_{50}$ values were determined and are shown in Tables 5-7.

TABLE 5

Inhibition of growth of HeLa, MCF7, MDAMB-231 and 293 cell lines.

| | Cell line inhibition of growth GI$_{50}$ (µM) | | | |
|---|---|---|---|---|
| Compound | HeLa | MCF7 | MDAMB-231 | 293 |
| 1 | 2.0 ± 1.0 | 4.0 ± 2.0 | 19 ± 8 | 92 ± 14 |
| 2 | 0.4 ± 0.3 | 0.5 ± 0.1 | 1.7 ± 0.3 | 5.1 ± 2.3 |
| 3 | 5.3 ± 2.5 | 6.6 ± 2.2 | 24 ± 10 | ND |
| 5 | 1.0 ± 0.3 | 2.3 ± 0.4 | 10 ± 1.8 | ND |
| 6 | 1.2 ± 0.2 | 1.9 ± 0.4 | 5.9 ± 2.6 | ND |
| 7 | 1.8 ± 0.6 | 3.6 ± 1.0 | 21 ± 11 | ND |

TABLE 6

Inhibition of growth of RPMI8226, RL, Molt4 and CCRF-CEM cell lines.

| | Cell line inhibition of growth GI$_{50}$ (µM) | | | |
|---|---|---|---|---|
| Compound | RPMI8226 | RL | Molt4 | CCRF-CEM |
| 1 | 1.1 ± 0.7 | 21 ± 10 | 7.4 ± 4.7 | 15 ± 5 |
| 2 | 0.4 ± 0.1 | 2.1 ± 1.1 | 1.1 ± 0.5 | 1.6 ± 0.8 |
| 3 | 1.2 ± 0.6 | 5.0 ± 2.0 | 2.7 ± 0.8 | 7.2 ± 4.3 |
| 5 | 9.8 ± 1.8 | 0.7 ± 0.2 | 0.6 ± 0.2 | 3.9 ± 1.3 |
| 6 | 1.2 ± 0.3 | 1.3 ± 0.4 | 0.7 ± 0.1 | 1.3 ± 0.4 |
| 7 | 3.4 ± 1.7 | 1.4 ± 0.7 | 1.2 ± 0.5 | 2.4 ± 1.1 |

TABLE 7

Inhibition of growth of HTC116 WT, HCT116 p53-/-, LNCaP, DU145 and PC3 cell lines.

| | Cell line inhibition of growth GI$_{50}$ (µM) | | | | |
|---|---|---|---|---|---|
| Compound | HTC116 WT | HCT116 p53-/- | LNCaP | DU145 | PC3 |
| 1 | 10 ± 2 | 12 ± 2 | 38 ± 8 | 18 ± 4 | 11 ± 1 |
| 2 | 2.4 ± 1.2 | 2.5 ± 1.5 | 2.7 ± 1.2 | 3.6 ± 1.5 | 2.2 ± 1.1 |
| 3 | 5.1 ± 2 | 4.0 ± 0.9 | 4.6 ± 1.1 | 8.2 ± 2.4 | 3.3 ± 0.9 |
| 4 | 19 ± 6 | 20 ± 5 | 23 ± 4 | 40 ± 10 | 6.3 ± 0.6 |
| 5 | 4.3 ± 1.8 | 12 ± 3 | 7.6 ± 1.7 | 3.5 ± 0.6 | 5.9 ± 0.5 |
| 6 | 2.8 ± 1.6 | 2.4 ± 1 | 2.5 ± 0.7 | 2.3 ± 0.7 | 0.3 ± 0.23 |
| 7 | 5.5 ± 1.4 | 13 ± 4 | 11 ± 4 | 4.9 ± 0.6 | 6.2 ± 1.2 |

Figure 21:
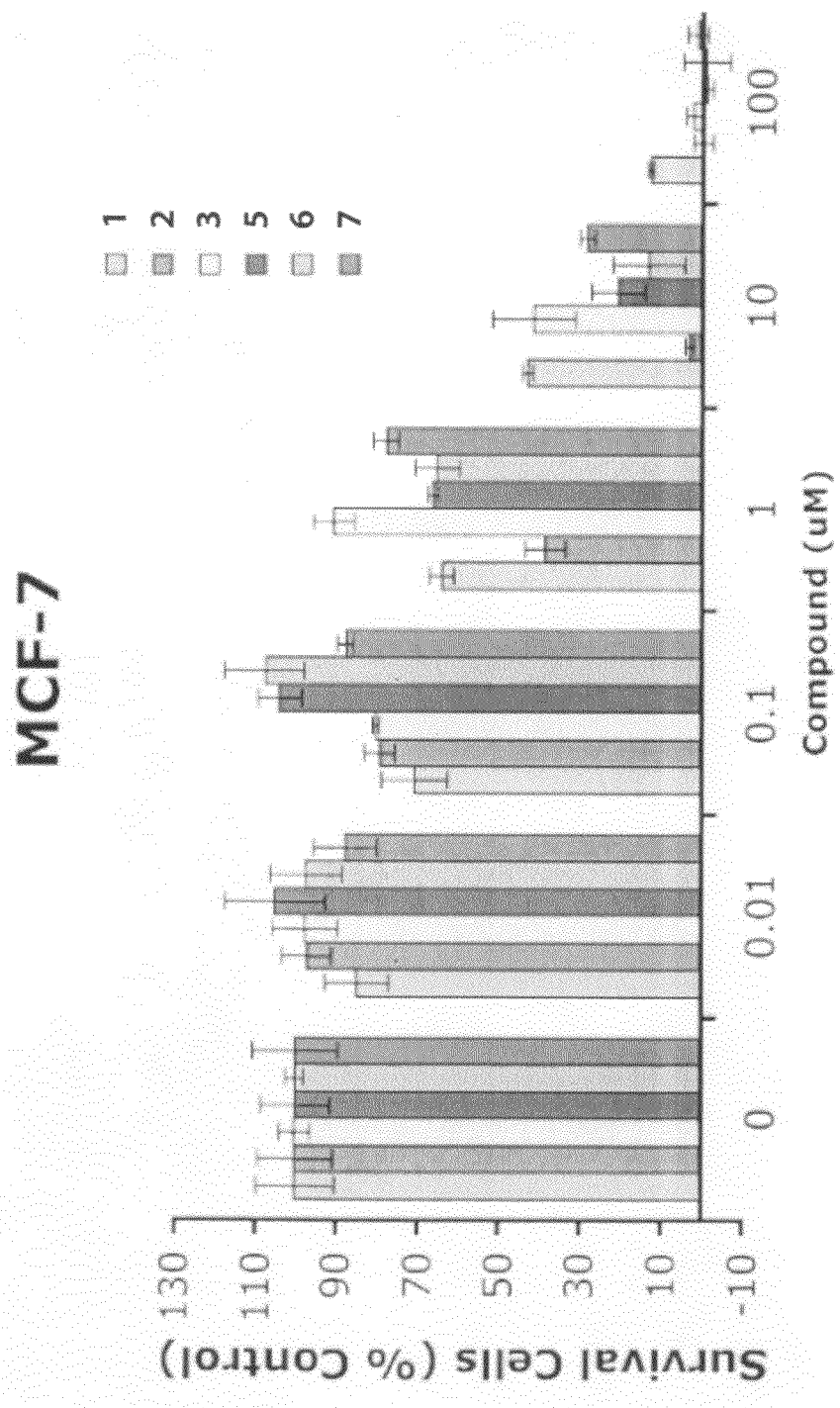
FIG. 21 shows a historgram of survival of MCF-7 cells treated with compounds of the disclosure.
Figure 22:
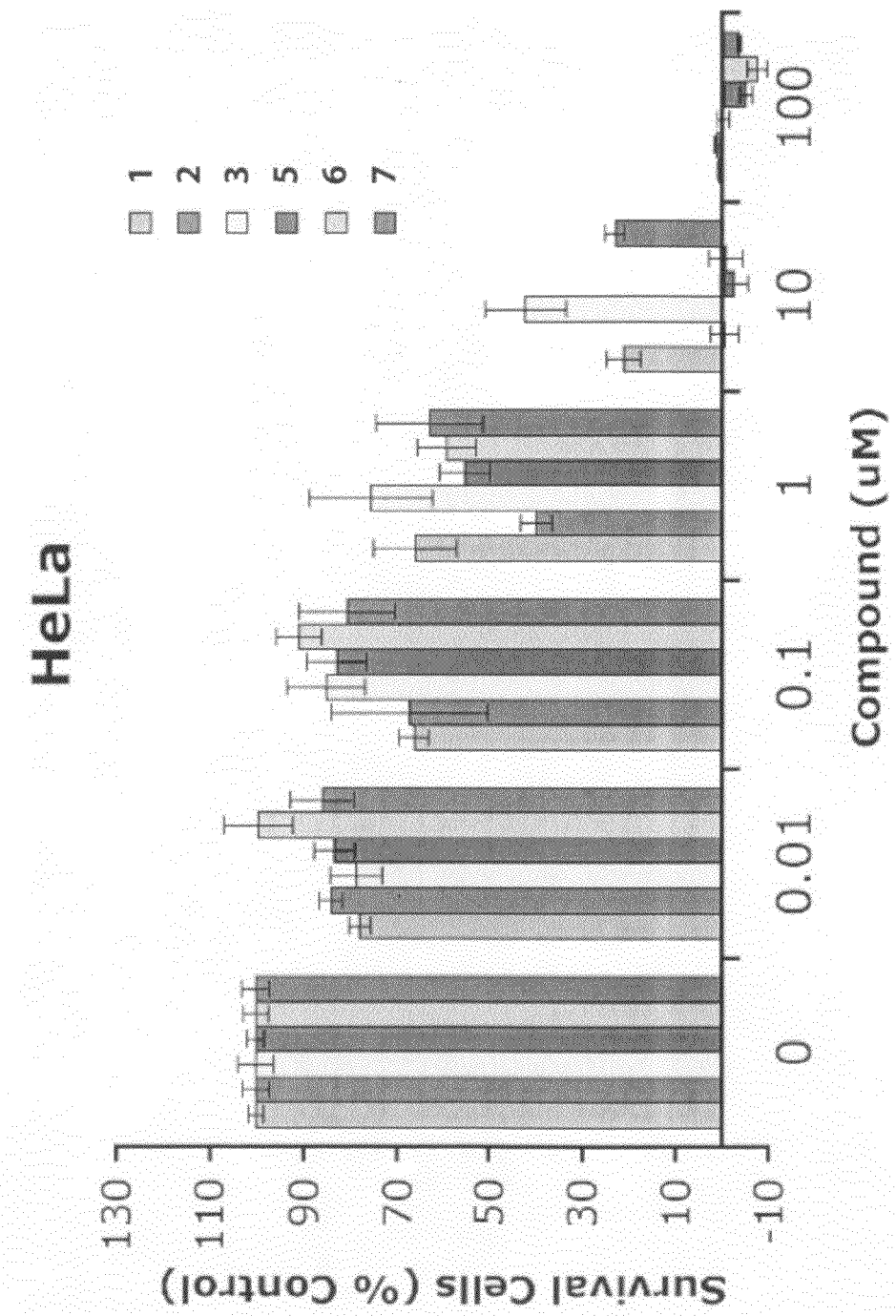
FIG. 22 shows a historgram of survival of HeLa cells treated with compounds of the disclosure.

Data for the assay with MCF-7 cells and HeLa cells is shown in FIG. 21 and FIG. 22, respectively. Of all the compounds tested, compound 2 appears to be the most potent, yielding 50% inhibition of growth (GI$_{50}$) at concentrations of compound 2 ranging from 0.4-5.1 µM across the 13 different cell lines. By contrast, the GI$_{50}$ for compound 1 was 3 to 18-fold higher across the same cell lines. Thus, compound 2 blocks p97-dependent processes in cells and also blocks the proliferation of cancer cell lines, illustrating its potential utility as an anti-proliferative drug to treat cancer.

Example 2

High-Throughput Screening to Identify Inhibitors of p97

An assay that measures the ATPase activity of p97 and that is amenable to high-throughput screening (HTS) was developed based on the commercially-available "Kinase-Glo" assay format, wherein the ATP hydrolytic activity of p97 is monitored by using luciferase to measure the level of residual ATP in a sample following incubation with p97. Using this assay, circa 16,000 compounds were screened to evaluate their effect on the ATP hydrolysis activity of p97. This effort yielded several candidates that inhibit p97 activity. Among the compounds that were identified, one that was of particular interest was compound 8 (9-(2-nitrovinyl) anthracene shown below:

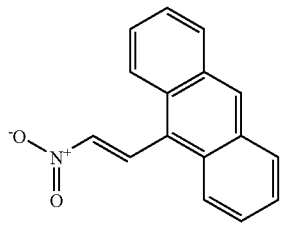

8

Figure 23:
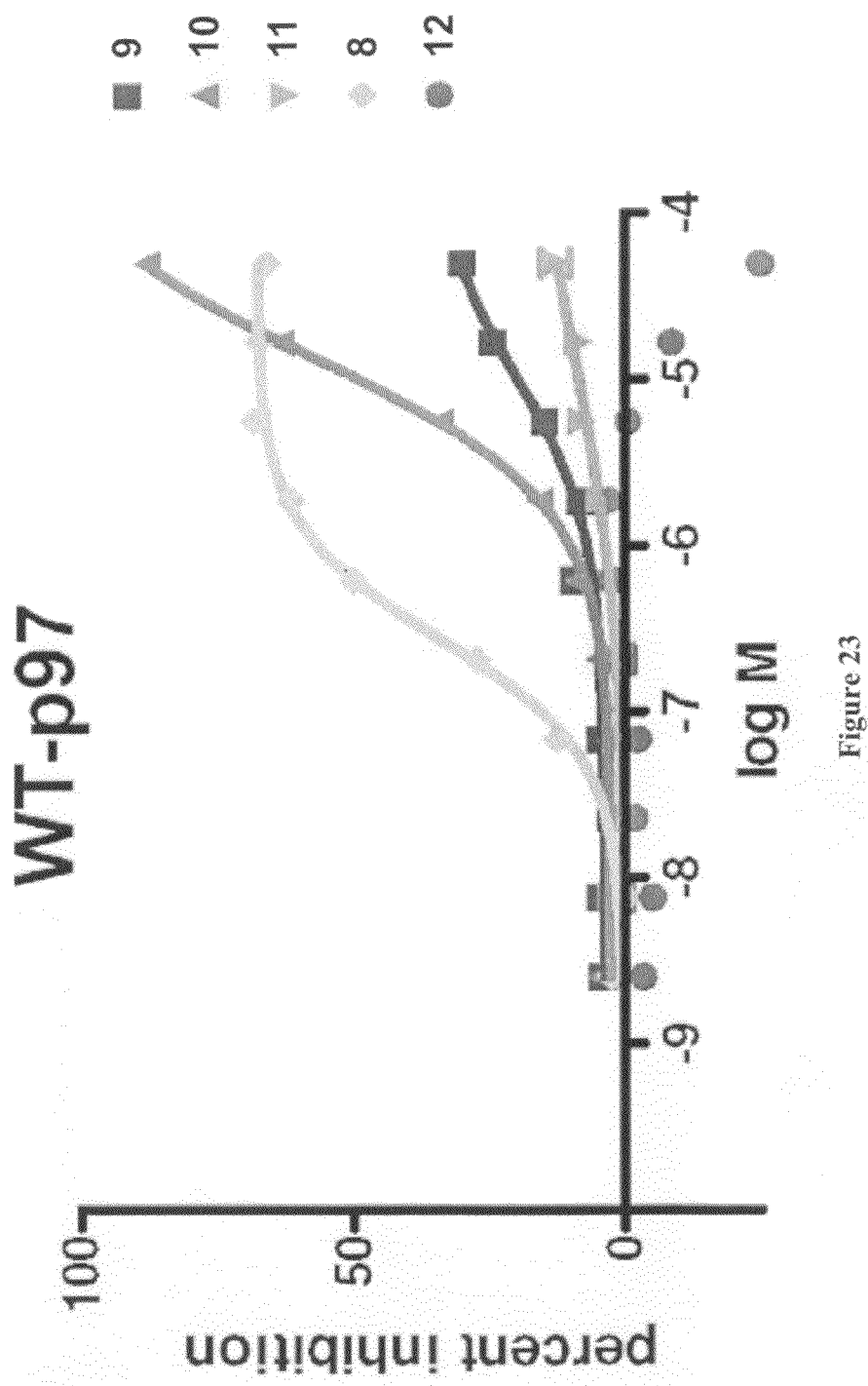
FIG. 23 shows a histogram of the inhibition of p97 in the presence of various compounds.
Figure 24:
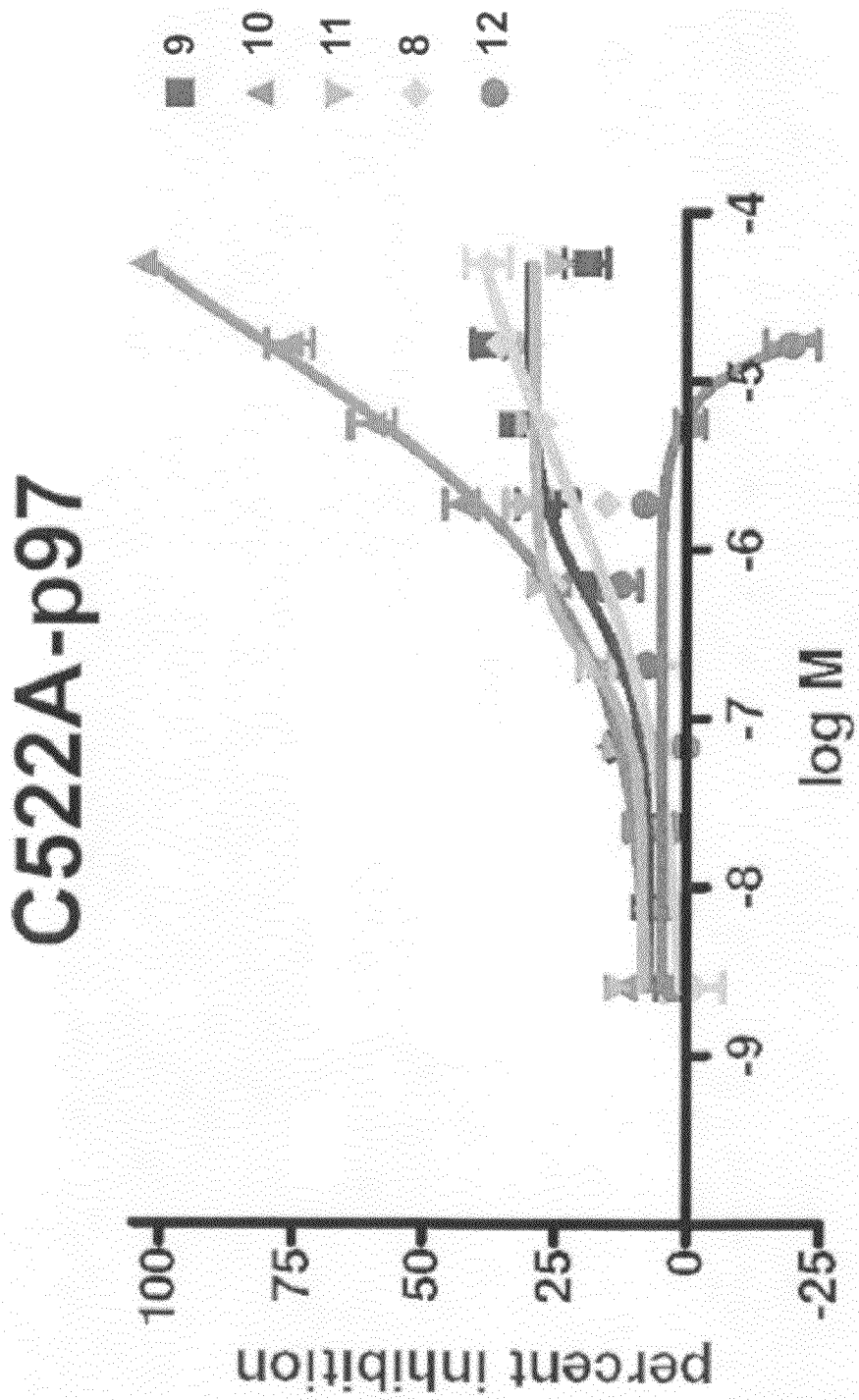
FIG. 24 shows a histogram of the inhibition of C522A-p97 in the presence of various compounds.

It was shown that a key feature of compound 8 is that its mode of inhibition is dependent upon the presence of a cysteine at position 522 in the D2 domain of p97. Compound 8 inhibited activity of wild type p97 (see FIG. 23) to a significantly greater degree than it did the C522A-p97 mutant as determined by the ATP Kinase glo assay (see FIG. 24).

Figure 25:
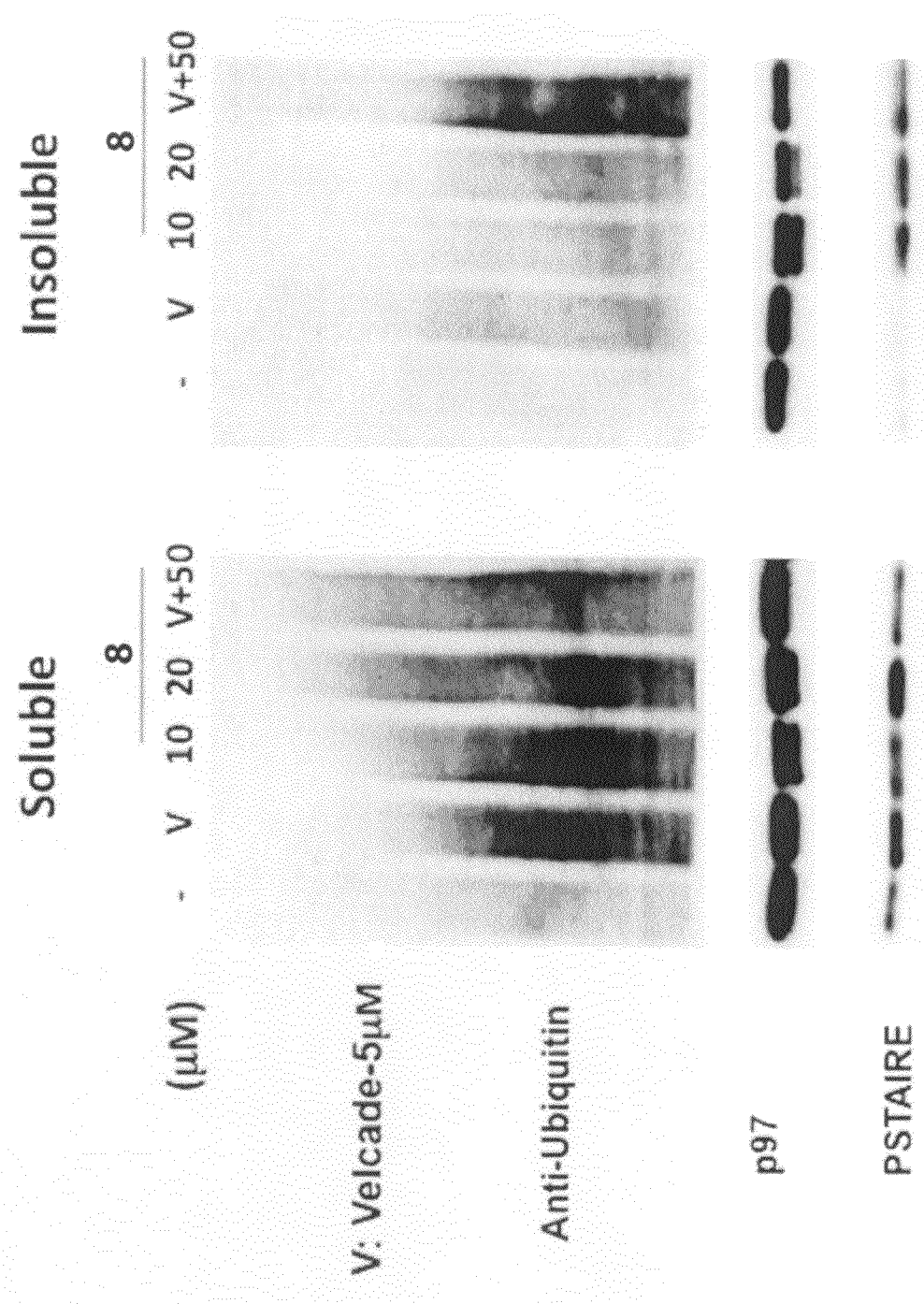
FIG. 25 shows results from a Western blot.
Figure 26:
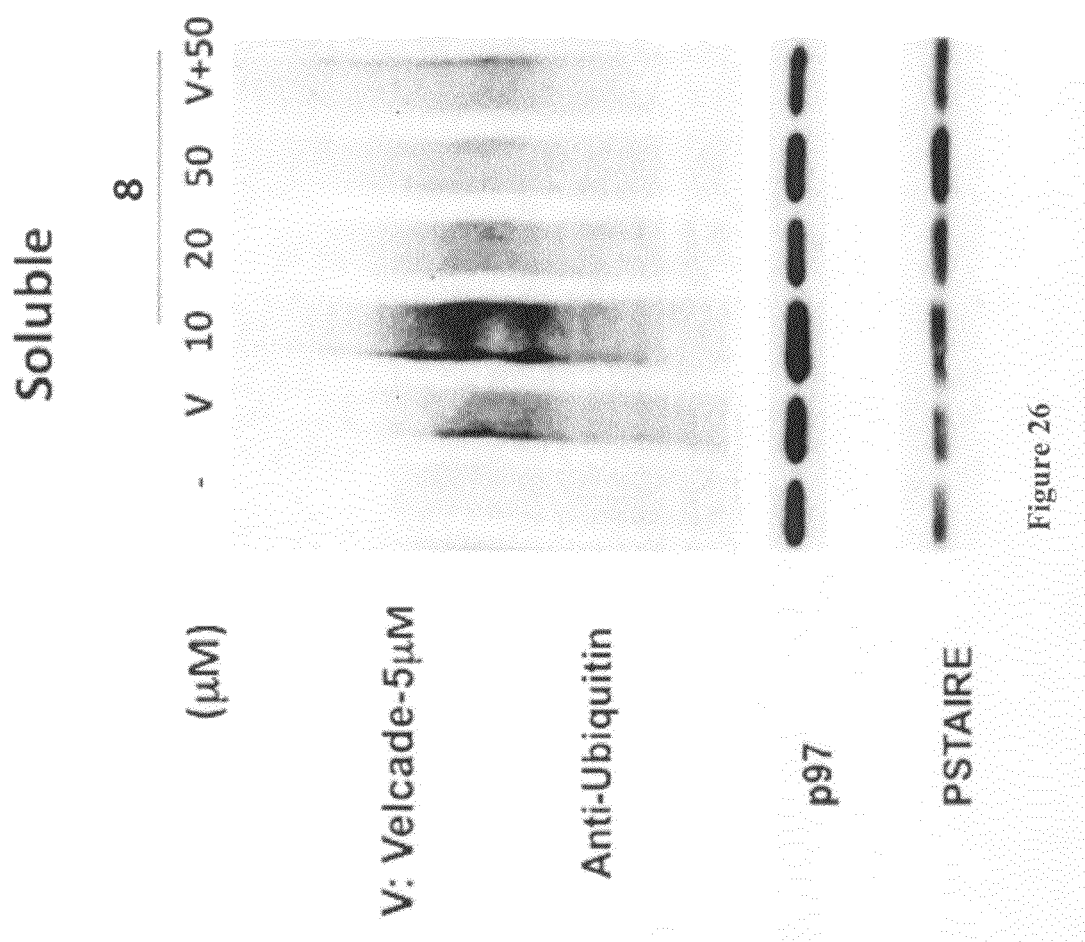
FIG. 26 shows results from a Western blot.

To evaluate whether compound 8 can target p97 activity in cells, it was determined whether this compound induces accumulation of high molecular weight ubiquitin conjugates, since it is known that RNAi-mediated knockdown of p97 in mammalian cells has this effect (Wojcik, C. et al. *J. Cell Sci.* (2004) 117, 281-292). The proteasome inhibitor bortezomib (velcade) was employed as a positive control for this experiment. HeLa (FIG. 25) or RPMI8226 (FIG. 26) cells were treated with Velcade, compound 8, or a combination thereof for 1 h at 37° C. The cells were then harvested and cell lysates were immunoblotted with anti-ubiquitin antibodies to detect accumulation of high molecular weight conjugates. Blots were also probed with anti-PSTAIRE antibodies as a loading control. The data revealed that compound 8 caused accumulation of high molecular weight ubiquitin conjugates.

Figure 27:
FIG. 27 shows fluorescence images of cells with Ub$_{G76V}$-GFP treated with DMSO, MG132, or compound 8.
Figure 27:
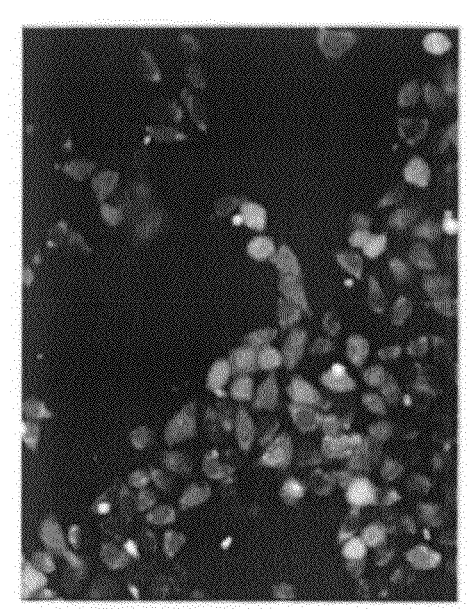
Figure 27:
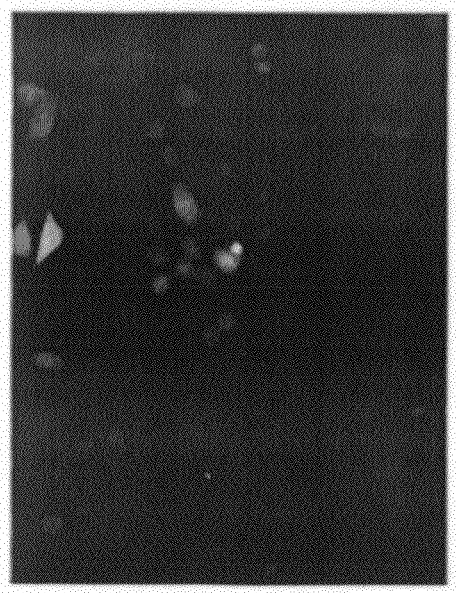
Figure 27:
Figure 28:
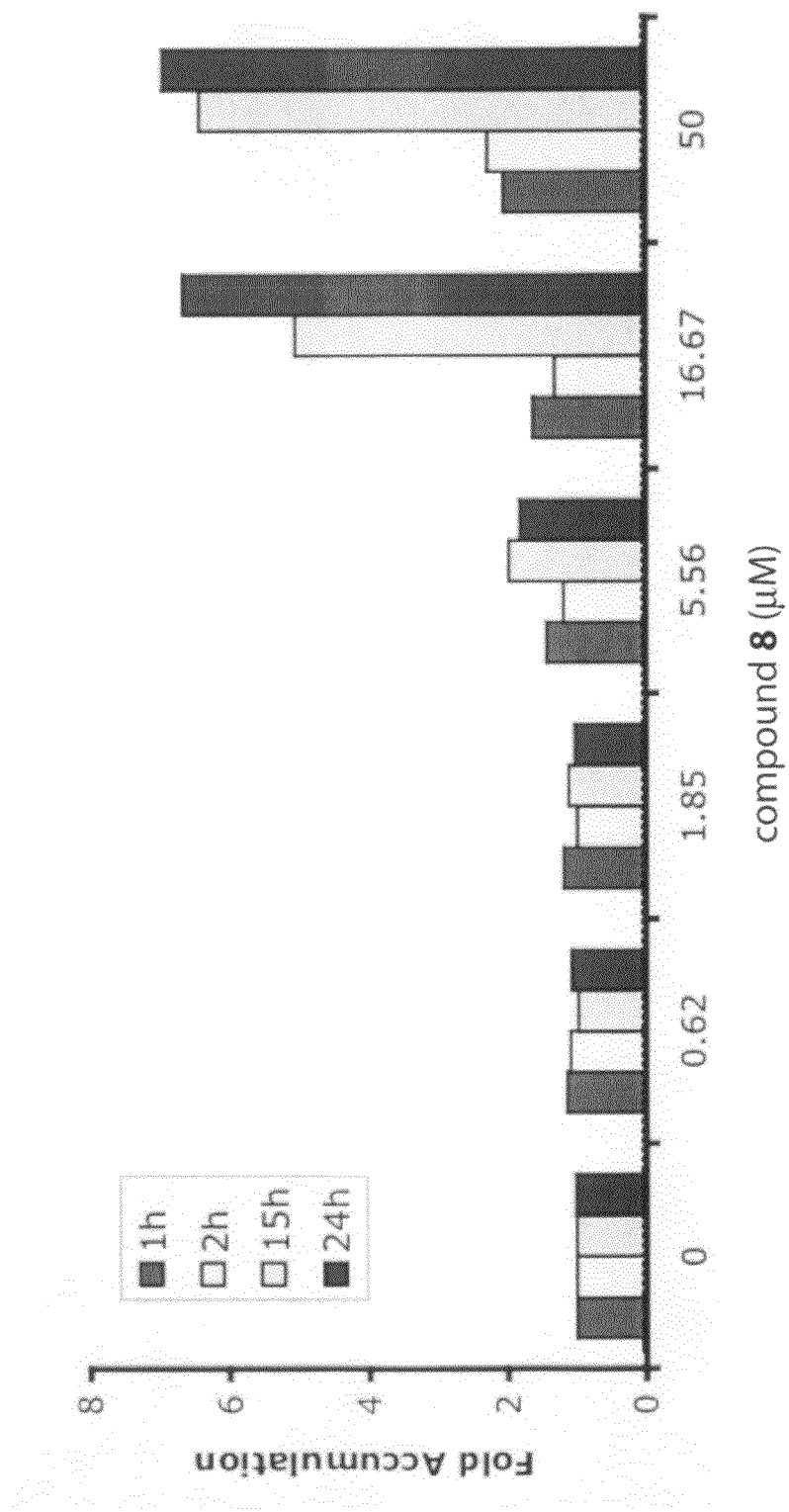
FIG. 28 shows a histogram that compares fluorescense data of cells treated with various councentrations of compound 8.

As a second test of whether compound 8 can inhibit p97 in vivo, it was evaluated whether it can cause accumulation of the $Ub_{G76V}$-GFP reporter. A HeLa cell line that stably expresses $Ub_{G76V}$-GFP was treated with compound 8 for 1 h at 37° C., and was then evaluated by fluorescence microscopy. As a control, the same cells were treated with the proteasome inhibitor MG132. Both MG132 and compound 8 caused detectable accumulation of $Ub_{G76V}$-GFP (FIG. 27), although the reporter exhibited a more punctuate pattern of accumulation in cells treated with compound 8. The level of GFP fluorescence was quantified in cells treated with compound 8 at different doses and for different periods of time (FIG. 28).

To determine whether compound 8 has an effect on turnover of accumulated reporter, the same cycloheximide chase experiment that was described in Example 1 was performed.

Figure 29:
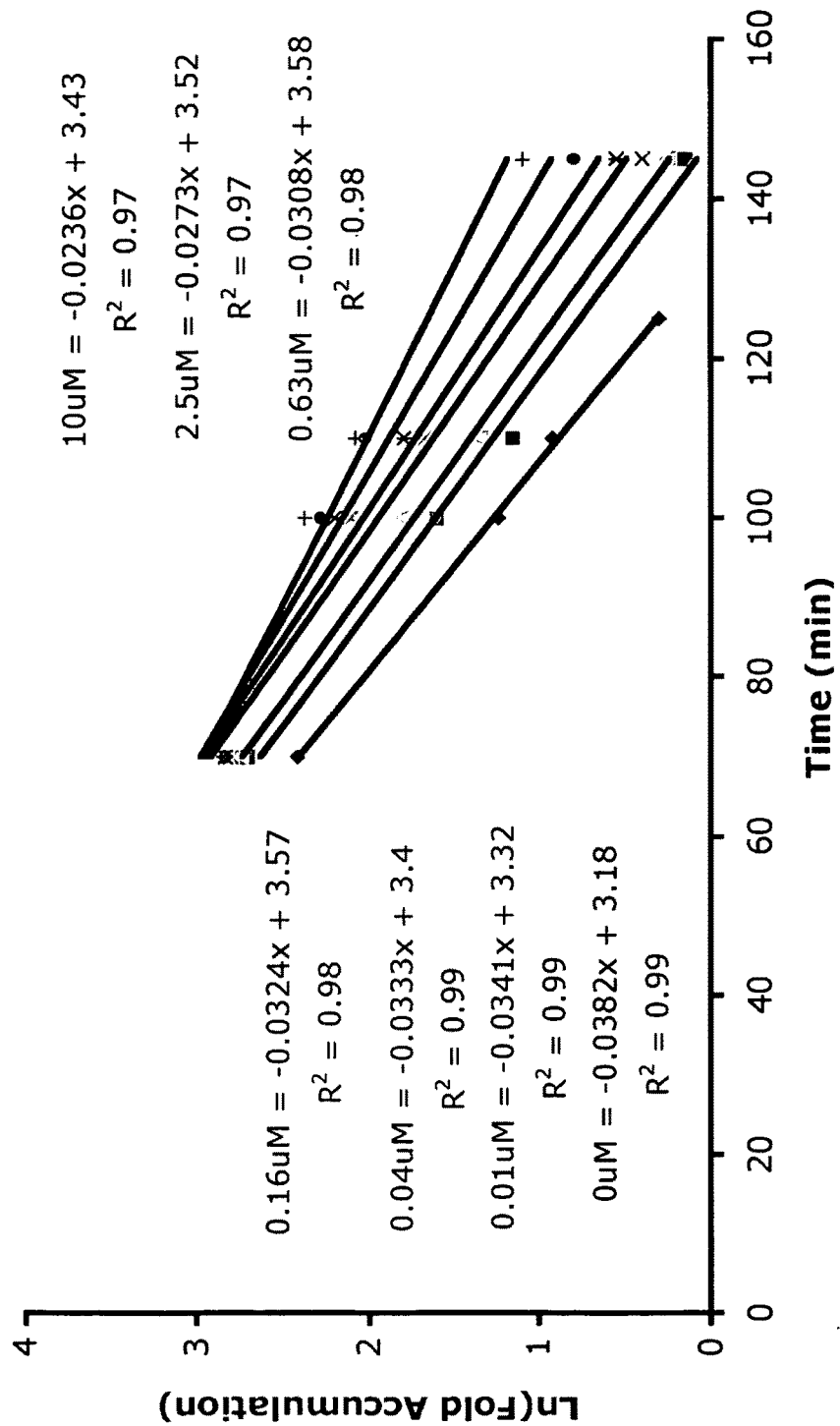
FIG. 29 shows a histogram of the rate of loss of accumulation of Ub$_{G76V}$-GFP in cells treated with compound 8.

$Ub_{G76V}$-GFP/HeLa cells were treated with MG132 (2 μM) for 1 h and washed with PBS three times. DMEM containing cycloheximide (50 μg/mL) and compound 8 (0-10 μM) was added into cells. Eight 96-well plates were prepared and one of the plates was imaged at 25, 50, 70, 100, 110, 125, 145, or 170 min after washing with PBS three times. Compound 8 inhibited turnover of accumulated $Ub_{G76V}$-GFP with an $IC_{50}$ value of 10±4 μM (see FIG. 29 and Table 8).

TABLE 8

Inhibition of $Ub_{G76V}$-GFP degradation by compound 8.

| Conc. Cmpd. 8 (μM) | K (1/min) | $t_{1/2}$ (min) = Ln(2)/k | % K |
|---|---|---|---|
| 0 | 0.038 | 18.1 | 100 |
| 0.01 | 0.034 | 20.3 | 89 |
| 0.04 | 0.033 | 20.8 | 87 |
| 0.16 | 0.032 | 21.4 | 85 |
| 0.63 | 0.031 | 22.5 | 81 |
| 2.5 | 0.027 | 25.4 | 71 |
| 10 | 0.023 | 30.1 | 60 |

$IC_{50}$ = 10 ± 4 μM

Figure 30:
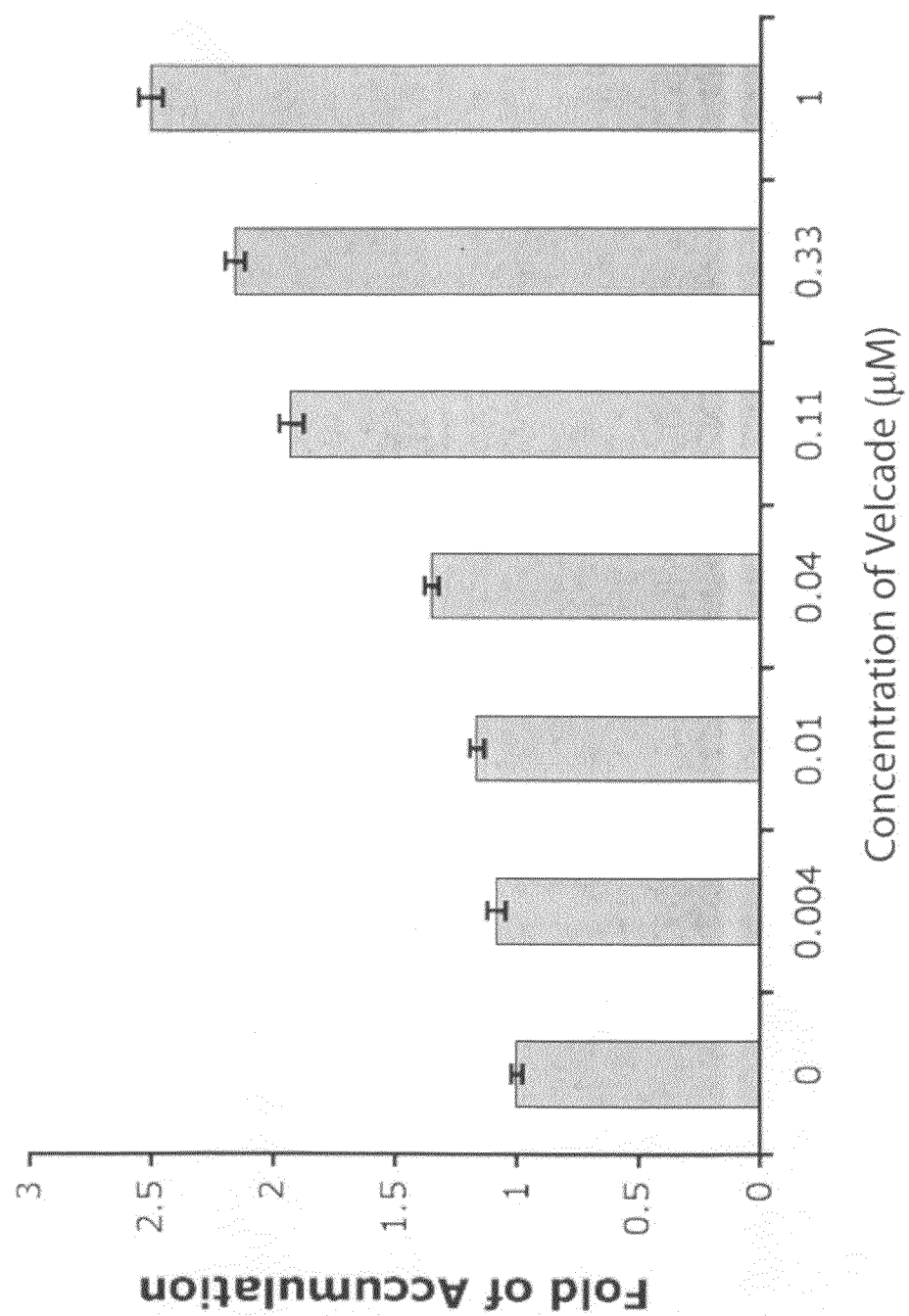
FIG. 30 shows a histogram that indicates accumulation of TCR-alpha-GFP in cells treated with various concentrations of Velcade.
Figure 31:
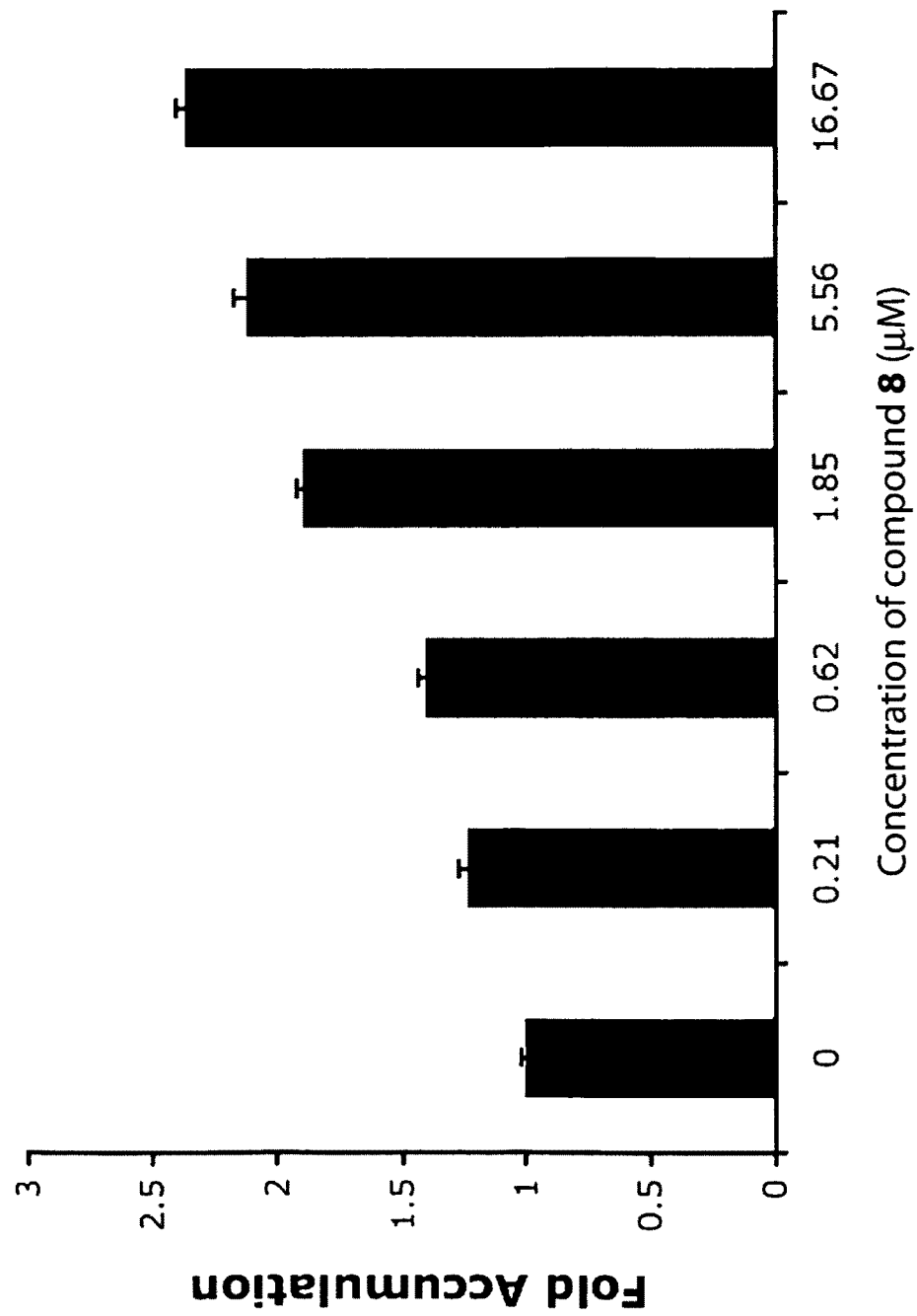
FIG. 31 shows a histogram that indicates accumulation of TCR-alpha-GFP in cells treated with various concentrations of compound 8.

Like compound 2, compound 8 also induced accumulation of the ERAD reporter, TCR-alpha-GFP. HEK293 cells that stably expressed TCR-GFP were treated with the Velcade (FIG. 30) or compound 8 (FIG. 31) at the indicated concentrations for 2 h at 37° C. prior to being imaged by fluorescence microscopy to quantify TCR-GFP accumulation. These data show that compound 8 inhibits p97 in cells, resulting in the accumulation of high molecular weight ubiquitin conjugates and UPS substrates whose degradation depends upon p97.

Figure 32:
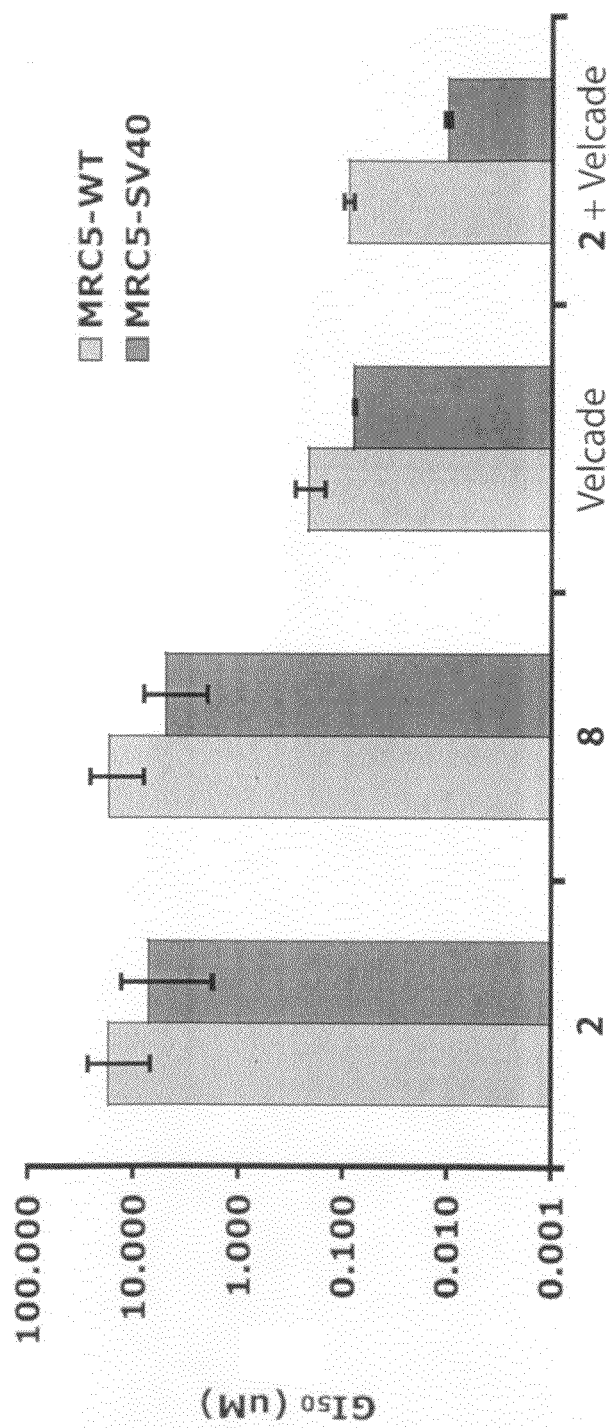
FIG. 32 shows a histogram indicating the GI$_{50}$ of cells treated with compound 2, compound 8, Velcade, or compound 2 and Velcade.

To compare the ability of compound 2 and compound 8 to selectively kill transformed cells, the concentration of compound required to inhibit growth of cells by 50% ($GI_{50}$) in cell culture assays was measured. Genetically matched parental MRC5 cells (WT) or cells engineered to express SV40 were treated with various compounds for 48 h at 37° C. and $GI_{50}$ values were determined by CellTiter-Glo assay (see FIG. 32 and).

TABLE 9

Inhibition of genetically matched cell lines.

| | Cell line inhibition of growth $GI_{50}$ (μM) | |
|---|---|---|
| Compound | MRC5-WT | MRC5-SV40 |
| 2 | 17 ± 10 | 7.3 ± 5.5 |
| 8 | 17 ± 9 | 5 ± 3 |
| Velcade | 0.2 ± 0.07 | 0.1 ± 0.01 |
| 2 + Velcade | 0.1 ± 0.01 | 0.01 ± 0.0006 |

The SV40-transformed cells were 2-fold and 3.4-fold more sensitive to the growth inhibitory effects of Compound 2 and Compound 8, respectively. Velcade also showed 2-fold greater potency towards the transformed cell line, whereas a combination of Compound 2 and Velcade blocked cell growth of the SV40-transformed cell line at a $GI_{50}$ 10-fold lower than that of the WT cell line. (FIG. 20)

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A method for treating cancer in a patient in need thereof, comprising inhibiting the activity of AAA p97 having the descriptive name, Valosin-containing protein, by contacting a cell with a therapeutically effective amount of a compound that binds to and inhibits p97, wherein the compound has a structure of formula (I):

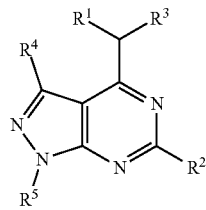

wherein $R^1$ is —C(O)—CH=CHR$^6$ or —C(O)—CH$_2$—X, X is chloro, $R^3$ is H or —C(O)—CH=CH$_2$, $R^2$ is hydrogen, $R^4$ is aryl, and $R^5$ is lower alkyl, or pharmaceutically acceptable salts thereof.

2. The method of claim 1, wherein the compound covalently binds to an active site of AAA p97 having the descriptive name Valosin-containing protein.

3. The method of claim 2, wherein the compound forms a covalent bond with a cysteine residue of the active site.

4. The method of claim 3, wherein the cysteine residue is Cys522.

5. The method according to claim 1 wherein $R^1$ has an atom susceptible to nucleophilic attack.

* * * * *

```
                           SEQUENCE LISTING

<160> NUMBER OF SEQ ID NOS: 8

<210> SEQ ID NO 1
<211> LENGTH: 10
<212> TYPE: PRT
<213> ORGANISM: Mus sp.

<400> SEQUENCE: 1

Tyr Gly Pro Pro Gly Thr Gly Lys Thr Leu
1               5                   10

<210> SEQ ID NO 2
<211> LENGTH: 10
<212> TYPE: PRT
<213> ORGANISM: Mus sp.

<400> SEQUENCE: 2

Tyr Gly Pro Pro Gly Cys Gly Lys Thr Leu
1               5                   10

<210> SEQ ID NO 3
<211> LENGTH: 10
<212> TYPE: PRT
<213> ORGANISM: Unknown
<220> FEATURE:
<223> OTHER INFORMATION: Description of Unknown: Unknown yeast peptide

<400> SEQUENCE: 3

Tyr Gly Pro Pro Gly Thr Gly Lys Thr Leu
1               5                   10

<210> SEQ ID NO 4
<211> LENGTH: 10
<212> TYPE: PRT
<213> ORGANISM: Unknown
<220> FEATURE:
<223> OTHER INFORMATION: Description of Unknown: Unknown hamster peptide

<400> SEQUENCE: 4

Tyr Gly Pro Pro Gly Cys Gly Lys Thr Leu
1               5                   10

<210> SEQ ID NO 5
<211> LENGTH: 10
<212> TYPE: PRT
<213> ORGANISM: Unknown
<220> FEATURE:
<223> OTHER INFORMATION: Description of Unknown: Unknown hamster peptide

<400> SEQUENCE: 5

Glu Gly Pro Pro His Ser Gly Lys Thr Ala
1               5                   10

<210> SEQ ID NO 6
<211> LENGTH: 10
<212> TYPE: PRT
<213> ORGANISM: Homo sapiens

<400> SEQUENCE: 6

Phe Gly Pro Pro Gly Thr Gly Lys Thr Leu
1               5                   10

<210> SEQ ID NO 7
```

```
<211> LENGTH: 10
<212> TYPE: PRT
<213> ORGANISM: Homo sapiens

<400> SEQUENCE: 7

Tyr Gly Pro Pro Gly Thr Gly Lys Thr Leu
1               5                   10

<210> SEQ ID NO 8
<211> LENGTH: 10
<212> TYPE: PRT
<213> ORGANISM: Homo sapiens

<400> SEQUENCE: 8

Tyr Gly Pro Pro Gly Cys Gly Lys Thr Met
1               5                   10
```